United States Patent
Thakur et al.

(10) Patent No.: US 10,660,577 B2
(45) Date of Patent: May 26, 2020

(54) SYSTEMS AND METHODS FOR DETECTING WORSENING HEART FAILURE

(71) Applicant: Cardiac Pacemakers, Inc., St. Paul, MN (US)

(72) Inventors: Pramodsingh Hirasingh Thakur, Woodbury, MN (US); Yi Zhang, Plymouth, MN (US); Qi An, Blaine, MN (US); Viktoria A. Averina, Shoreview, MN (US)

(73) Assignee: Cardiac Pacamakers, Inc., St. Paul, MN (US)

( * ) Notice: Subject to any disclaimer, the term of this patent is extended or adjusted under 35 U.S.C. 154(b) by 310 days.

(21) Appl. No.: 15/473,783

(22) Filed: Mar. 30, 2017

(65) Prior Publication Data

US 2017/0281097 A1    Oct. 5, 2017

Related U.S. Application Data

(60) Provisional application No. 62/316,905, filed on Apr. 1, 2016.

(51) Int. Cl.
*A61B 5/00*    (2006.01)
*A61N 1/365*   (2006.01)
(Continued)

(52) U.S. Cl.
CPC .......... *A61B 5/7275* (2013.01); *A61B 5/0205* (2013.01); *A61B 5/091* (2013.01);
(Continued)

(58) Field of Classification Search
CPC ... A61B 5/0205; A61B 5/0816; A61B 5/7275; A61B 5/0031; A61B 5/686;
(Continued)

(56) References Cited

U.S. PATENT DOCUMENTS 6,549,804 B1    4/2003 Osorio et al.
7,494,459 B2    2/2009 Anstadt et al.
(Continued)

FOREIGN PATENT DOCUMENTS

CN    109069060 A     12/2018
IN    201817040534 A   2/2019
(Continued)

OTHER PUBLICATIONS

"Australian Application Serial No. 2017240582, First Examination Report dated Jan. 23, 2019", 3 pgs.
(Continued)

*Primary Examiner* — Sean P Dougherty
*Assistant Examiner* — Benjamin S Melhus
(74) *Attorney, Agent, or Firm* — Schwegman Lundberg & Woessner, P.A.

(57) ABSTRACT

Systems and methods for detecting worsening cardiac conditions such as worsening heart failure events are described. A system may include sensor circuits to sense physiological signals and signal processors to generate from the physiological signals first and second signal metrics. The system may include a risk stratifier circuit to produce a cardiac risk indication. The system may use at least the first signal metric to generate a primary detection indication, and use at least the second signal metric and the risk indication to generate a secondary detection indication. The risk indication may be used to modulate the second signal metric. A detector circuit may detect the worsening cardiac event using the primary and secondary detection indications.

20 Claims, 9 Drawing Sheets

(51) Int. Cl.

| | | |
|---|---|---|
| *A61B 5/0205* | (2006.01) | |
| *A61N 1/362* | (2006.01) | |
| *A61B 5/091* | (2006.01) | |
| *G16H 40/63* | (2018.01) | |
| *G16H 50/30* | (2018.01) | |
| *G16H 50/20* | (2018.01) | |
| *A61B 5/08* | (2006.01) | |
| *A61B 7/04* | (2006.01) | |

(52) U.S. Cl.
CPC ............ *A61B 5/4836* (2013.01); *A61B 5/686* (2013.01); *A61B 5/7264* (2013.01); *A61B 5/7282* (2013.01); *A61B 5/746* (2013.01); *A61N 1/3627* (2013.01); *A61N 1/36585* (2013.01); *G16H 40/63* (2018.01); *G16H 50/20* (2018.01); *G16H 50/30* (2018.01); *A61B 5/0816* (2013.01); *A61B 7/04* (2013.01)

(58) Field of Classification Search
CPC ..... A61B 5/0022; A61B 5/0538; A61B 5/091; A61B 5/1118; A61B 5/0002; A61B 5/0008; A61B 5/01; A61B 5/02007; 5/02028; A61B 5/02055; A61B 5/0215; A61B 5/024; A61B 5/02405; A61B 5/026; A61B 5/029; A61B 5/042; A61B 5/0452; A61B 5/046; A61B 5/0464; A61B 5/0507; A61B 5/0531; A61B 5/0803; A61B 5/085; A61B 5/087; A61B 5/1075; A61B 5/1135; A61B 5/121; A61B 5/14542; A61B 5/4836; A61B 5/4842; A61B 5/4875; A61B 5/6804; A61B 5/6805; A61B 5/6831; A61B 5/6833; A61B 5/6869; A61B 5/7264; A61B 5/7282; A61B 5/746
See application file for complete search history.

(56) References Cited

U.S. PATENT DOCUMENTS

| | | |
|---|---|---|
| 7,899,545 B2 | 3/2011 | John |
| 8,587,426 B2 | 11/2013 | Bloem |
| 8,740,789 B2 | 6/2014 | Brockway et al. |
| 8,821,418 B2 | 9/2014 | Meger et al. |
| 8,838,222 B2 | 9/2014 | Narayan et al. |
| 8,838,223 B2 | 9/2014 | Narayan et al. |
| 8,838,246 B2 | 9/2014 | Kieval |
| 8,858,432 B2 | 10/2014 | Robertson et al. |
| 8,862,196 B2 | 10/2014 | Lynn |
| 8,862,229 B2 | 10/2014 | Stahmann |
| 8,868,169 B2 | 10/2014 | Narayan et al. |
| 8,880,190 B2 | 11/2014 | Kieval et al. |
| 8,911,369 B2 | 12/2014 | Brister et al. |
| 8,926,509 B2 | 1/2015 | Magar et al. |
| 8,928,671 B2 | 1/2015 | Adler et al. |
| 8,929,968 B2 | 1/2015 | Brister et al. |
| 8,932,227 B2 | 1/2015 | Lynn |
| 8,956,304 B2 | 2/2015 | Schecter |
| 8,996,108 B2 | 3/2015 | McCabe et al. |
| 9,002,427 B2 | 4/2015 | Tupin, Jr. et al. |
| 9,020,572 B2 | 4/2015 | Mensinger et al. |
| 9,020,593 B2 | 4/2015 | Arcot-Krishnamurthy et al. |
| 9,037,239 B2 | 5/2015 | Brooke et al. |
| 9,042,952 B2 | 5/2015 | Lynn et al. |
| 9,044,182 B2 | 6/2015 | Silver |
| 9,044,609 B2 | 6/2015 | Bolea et al. |
| 9,083,589 B2 | 7/2015 | Arne et al. |
| 9,089,269 B2 | 7/2015 | Narayan et al. |
| 9,095,554 B2 | 8/2015 | Lewis et al. |
| 9,132,217 B2 | 9/2015 | Soykan et al. |
| 9,143,569 B2 | 9/2015 | Mensinger et al. |
| 2006/0247702 A1 | 11/2006 | Stegemann et al. |
| 2007/0208263 A1 | 9/2007 | John et al. |
| 2008/0061961 A1 | 3/2008 | John et al. |
| 2008/0161657 A1 | 7/2008 | Bullens et al. |
| 2008/0188763 A1 | 8/2008 | John et al. |
| 2008/0288023 A1 | 11/2008 | John |
| 2011/0060215 A1 | 3/2011 | Tupin, Jr. et al. |
| 2013/0116578 A1* | 5/2013 | An .................... A61B 5/0205 600/484 |
| 2013/0211855 A1* | 8/2013 | Eberle ............... A61N 1/37282 705/3 |
| 2014/0201627 A1 | 7/2014 | Freeman et al. |
| 2015/0157221 A1 | 6/2015 | An et al. |
| 2015/0250428 A1 | 9/2015 | Zhang et al. |

FOREIGN PATENT DOCUMENTS

| | | |
|---|---|---|
| JP | 2019513440 A | 5/2019 |
| WO | WO-2013177621 A1 | 12/2013 |
| WO | WO-2015065674 A1 | 5/2015 |
| WO | WO-2015175207 A1 | 11/2015 |
| WO | WO-2017173014 A1 | 10/2017 |

OTHER PUBLICATIONS

"Australian Application Serial No. 2017240582, Response Filed Jun. 24, 2019 to First Examination Report dated Jan. 23, 2019", 8 pgs.

"European Application Serial No. 17717046.1, Response Filed May 24, 2019 to Communication pursuant to Rules 161(2) and 162 EPC dated Nov. 16, 2018", 14 pgs.

"International Application Serial No. PCT/US2017/024889, International Preliminary Report on Patentability dated Oct. 11, 2018", 10 pgs.

"International Application Serial No. PCT/US2017/024889, International Search Report dated Jun. 30, 2017", 5 pgs.

"International Application Serial No. PCT/US2017/024889, Written Opinion dated Jun. 30, 2017", 10 pgs.

* cited by examiner

SYSTEMS AND METHODS FOR DETECTING WORSENING HEART FAILURE

CLAIM OF PRIORITY

This application claims the benefit of priority under 35 U.S.C. § 119(e) of U.S. Provisional Patent Application Ser. No. 62/316,905, filed on Apr. 1, 2016, which is herein incorporated by reference in its entirety.

TECHNICAL FIELD

This document relates generally to medical devices, and more particularly, to systems, devices and methods for detecting and monitoring events indicative of worsening of congestive heart failure.

BACKGROUND

Congestive heart failure (CHF or HF) is a major health problem and affects many people in the United States alone. CHF patients may have enlarged heart with weakened cardiac muscles, resulting in poor cardiac output of blood. Although CHF is usually a chronic condition, it may occur suddenly. It may affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

In many CHF patients, elevated pulmonary vascular pressures may cause fluid accumulation in the lungs over time. The fluid accumulation may precede or coincide with worsening of HF such as episodes of HF decompensation. The HF decompensation may be characterized by pulmonary or peripheral edema, reduced cardiac output, and symptoms such as fatigue, shortness of breath, and the like.

SUMMARY

Ambulatory medical devices may be used for monitoring HF patient and detecting worsening cardiac conditions such as a worsening heart failure (WHF) event. Examples of such ambulatory medical devices may include implantable medical devices (IMD), subcutaneous medical devices, wearable medical devices or other external medical devices. The ambulatory medical devices may include physiological sensors which may be configured to sense electrical activity and mechanical function of the heart. The ambulatory medical devices may deliver therapy such as electrical stimulations to target tissues or organs, such as to restore or improve the cardiac function. Some of these devices may provide diagnostic features, such as using transthoracic impedance or other sensor signals to detect a disease or a disease condition. For example, fluid accumulation in the lungs decreases the transthoracic impedance due to the lower resistivity of the fluid than air in the lungs.

Detection of worsening cardiac conditions may be based on a detected change of a sensor signal (such as a thoracic impedance signal) from a reference signal. An ideal detector of worsening cardiac conditions, such as a WHF event, may have one or more of a high sensitivity, a high specificity, a low false positive rate (FPR), or a high positive predictive value (PPV). The sensitivity may be represented as a percentage of actual WHF events that are correctly recognized by a detection method. The specificity may be represented as a percentage of actual non-WHF events that are correctly recognized as non-WHF events by the detection method. The FPR may be represented as a frequency of false positive detections of WHF events per patient within a specified time period (e.g., a year). The PPV may be represented as a percentage of the detected WHF events, as declared by the detection method, which are actual WHF events. A high sensitivity may help ensure timely intervention to a patient with an impending WHF episode, whereas a high specificity and a high PPV may avoid unnecessary intervention and reduce false alarms.

Frequent monitoring of CHF patients and timely and accurate detection of WHF events may reduce cost associated with HF hospitalization. CHF patients, however, may be exposed to different degrees of risks of developing a future WHF event. Therefore, identification of patients at relatively higher risks may ensure more effective and timely treatment, improve the prognosis and patient outcome, and avoid unnecessary medical intervention and reduce healthcare cost.

This document discusses, among other things, a patient management system for detecting worsening cardiac events such as WHF events that based at least on identified patient risks of developing future WHF events. The system discussed herein may include sensor circuits to sense physiological signals and processors to generate from the physiological signals first and second signal metrics. The system may include a risk stratifier circuit to produce a cardiac risk indication. The system may use at least the first signal metric to generate a primary detection indication, and use at least the second signal metric and the risk indication to generate a secondary detection indication. The risk indication may be used to modulate the second signal metric. A detector circuit may detect the worsening cardiac event using the primary and secondary detection indications.

In Example 1, a system for detecting a worsening cardiac event in a patient is disclosed. The system may comprise sensor circuits including sense amplifier circuits to sense a first physiological signal and a second physiological signal, a signal processor circuit configured to generate a first signal metric from the first physiological signal and a second signal metric from the second physiological signal, a risk stratifier circuit configured to produce a risk indication indicating a risk of the patient developing a future worsening cardiac event, and a detector circuit coupled to the signal processor circuit and the risk stratifier circuit. The detector circuit may be configured to generate a primary detection indication using at least the first signal metric and a secondary detection indication using at least the second signal metric and the risk indication, and to detect the worsening cardiac event using the primary and secondary detection indications.

Example 2 may include, or may optionally be combined with the subject matter of Example 1 to optionally include, an output circuit that may generate an alert in response to the detection of the worsening cardiac event.

Example 3 may include, or may optionally be combined with the subject matter of one or any combination of Examples 1 or 2 to include, the first signal metric that may include a heart sound signal metric and the second signal metric includes a respiratory signal metric. The heart sound signal metric may include a third heart sound (S3) intensity or a ratio of a third heart sound (S3) intensity to a reference heart sound intensity, and the respiratory signal metric may include a respiration rate measurement, a tidal volume measurement, or a ratio of the respiration rate to the tidal volume measurement.

Example 4 may include, or may optionally be combined with the subject matter of one or any combination of Examples 1 through 3 to include, the detector circuit that may detect the worsening cardiac event using a decision tree including the primary and secondary detection indications. The secondary detection indication may be generated based on a sub-decision tree included in the decision tree. The sub-decision tree may include the risk indication and a detection based on at least the second signal metric.

Example 5 may include, or may optionally be combined with the subject matter of Example 4 to optionally include, the sensor circuits that may further include a third sense amplifier circuit to sense a third physiological signal and the sub-decision tree that may further include a detection based on the third physiological signal. The detector circuit may be configured to generate the secondary detection indication using the risk indication if the decision based on the second physiological signal indicates a detection of the worsening cardiac event, or generate the secondary detection indication using the detection based on the third physiological signal if the decision based on the second physiological signal indicates no detection of the worsening cardiac event.

Example 6 may include, or may optionally be combined with the subject matter of one or any combination of Examples 1 through 5 to include, the primary or secondary detection indication that may include a Boolean-logic or fuzzy-logic combination of two or more signal metrics, or the risk indication that may include a Boolean-logic or fuzzy-logic combination of two or more risk indications.

Example 7 may include, or may optionally be combined with the subject matter of one or any combination of Examples 1 through 6 to include, the detector circuit that may generate a composite signal trend using a combination of the first signal metric and the second signal metric modulated by the risk indication, and detect the worsening cardiac event in response to the composite signal trend satisfying a specified condition.

Example 8 may include, or may optionally be combined with the subject matter of Example 7 to optionally include, the modulation of the second signal metric that may include a temporal change of the second signal metric weighted by the risk indication.

Example 9 may include, or may optionally be combined with the subject matter of Example 7 to optionally include, the modulation of the second signal metric that may include a temporal change of the second signal metric sampled when the risk indication satisfies a specified condition.

Example 10 may include, or may optionally be combined with the subject matter of one or any combination of Examples 1 through 9 to include, the second signal metric that is more sensitive and less specific to the worsening cardiac event than the first signal metric.

In Example 11, a system for identifying a patient's risk of developing a future worsening cardiac disease is disclosed. The system may comprise sensor circuits, a signal processor circuit, a risk stratifier circuit coupled to the signal processor circuit, and an output circuit. The sensor circuits may include sense amplifier circuits to sense first, second, and third physiological signals. The signal processor circuit may generate a first signal metric from the first physiological signal, a second signal metric from the second physiological signal, and a third signal metric from the second physiological signal. The risk stratifier circuit generate a primary cardiac risk indication using at least the first signal metric, a secondary cardiac risk indication using at least the second and third signal metrics, and a composite cardiac risk indication using both the primary and secondary cardiac risk indications. The output circuit may provide the composite cardiac risk indication to a clinician or a process.

Example 12 may include, or may optionally be combined with the subject matter of Example 11 to optionally include, the risk stratifier circuit that may generate a secondary cardiac risk indication using a plurality of measurements of the second signal metric during a time period when the third signal metric satisfies a specified condition.

Example 13 may include, or may optionally be combined with the subject matter of one or any combination of Examples 11 or 12 to include, the signal processor circuit that may generate a first plurality of measurements of the first signal metric and a second plurality of measurements of the second signal metric. The risk stratifier circuit may generate the primary cardiac risk indication including a first statistic of the first plurality of measurements of the first signal metric, and the secondary cardiac risk indication including a second statistic of the second plurality of measurements of the second signal metric. The risk stratifier circuit may generate the composite cardiac risk indication using a combination of the first statistic of the first signal metric and the second statistic of the second signal metric.

Example 14 may include, or may optionally be combined with the subject matter of one or any combination of Examples 11 through 13 to include, a fusion model selector circuit that may select a fusion model from a plurality of candidate fusion models based on signal quality of the first, second, and third physiological signals. The risk stratifier circuit may generate the composite cardiac risk indication using both the primary and secondary cardiac risk indications according to the selected fusion model.

Example 15 may include, or may optionally be combined with the subject matter of one or any combination of Examples 11 through 14 to include, the risk stratifier circuit that may transform the composite cardiac risk indication using a sigmoid function.

In Example 16, a method for detecting a worsening cardiac event in a patient is disclosed. The method may include steps of sensing, via sensor circuits, first and second physiological signals; generating a first signal metric from the first physiological signal and a second signal metric from the second physiological signal; producing a risk indication indicating a risk of the patient developing a future worsening cardiac event; generating a primary detection indication using at least the first signal metric, and a secondary detection indication using at least the second signal metric and the risk indication; and detecting the worsening cardiac event using the primary and secondary detection indications.

Example 17 may include, or may optionally be combined with the subject matter of Example 16 to optionally include, the method of detecting the worsening cardiac event including using a decision tree based on the primary and secondary detection indications. The decision tree may include a sub-decision tree based on the risk indication and a detection based on at least the second signal metric.

Example 18 may include, or may optionally be combined with the subject matter of Example 16 to optionally include, the primary or secondary detection indication that may include a Boolean-logic or fuzzy-logic combination of two or more signal metrics, or the risk indication includes a Boolean-logic or fuzzy-logic combination of two or more risk indications.

Example 19 may include, or may optionally be combined with the subject matter of Example 16 to optionally include, steps of generating a composite signal trend using a combination of the first signal metric and the second signal metric modulated by the risk indication, wherein the worsening cardiac event is detected in response to the composite signal trend satisfying a specified condition.

Example 20 may include, or may optionally be combined with the subject matter of Example 19 to optionally include, the modulation of the second signal metric that may include a scaled temporal change of the second signal metric weighted by the risk indication, or a sampled temporal change of the second signal metric when the risk indication satisfies a specified condition.

Example 21 may include, or may optionally be combined with the subject matter of Example 16 to optionally include, the method of producing the risk indication that may include generating a primary cardiac risk indication using at least a first signal metric for cardiac risk assessment and a secondary cardiac risk indication using at least second and third signal metrics for cardiac risk assessment, and generating a composite cardiac risk indication using both the primary and secondary cardiac risk indications.

Example 22 may include, or may optionally be combined with the subject matter of Example 21 to optionally include, the method of generating the secondary cardiac risk indication which may include taking a plurality of measurements of the second signal metric during a time period when the third signal metric satisfies a specified condition.

Example 23 may include, or may optionally be combined with the subject matter of Example 21 to optionally include, the method of producing the risk indication that may include transforming the composite cardiac risk indication using a sigmoid function.

The systems, devices, and methods discussed in this document may improve the medical technology of automated monitoring of patients with worsening heart failure (WHF). The detection of WHF based on primary and secondary detections and a cardiac risk indication may enhance the performance and functionality of a medical system or an ambulatory medical device for detecting WHF. In certain examples, the enhanced device functionality may include more timely detection of WHF with increased accuracy (e.g., lower false positive rate and higher positive predictive value) at little to no additional cost. The improvement in system performance and functionality, provided by the present systems and methods, can reduce healthcare costs associated with management and hospitalization of heart failure patients. The systems, devices, and methods discussed in this document also allow for more efficient device memory usage, such as by storing cardiac risk indications and signal metrics that are clinically more relevant to WHF. As fewer false positive detections are provided, device battery life can be extended, fewer unnecessary drugs and procedures may be scheduled, prescribed, or provided, and an overall system cost savings may be realized.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting worsening cardiac conditions, including events indicative of worsening heart failure. The WHF event may occur before systematic manifestation of worsening of HF. The systems, devices, and methods described herein may be used to determine a patient's cardiac status as well as to track progression of the cardiac condition such as worsening of a HF event. This system may also be used in the context of HF comorbidities and worsening chronic diseases such as pulmonary congestion, pneumonia, or renal diseases, among others.

Figure 1:
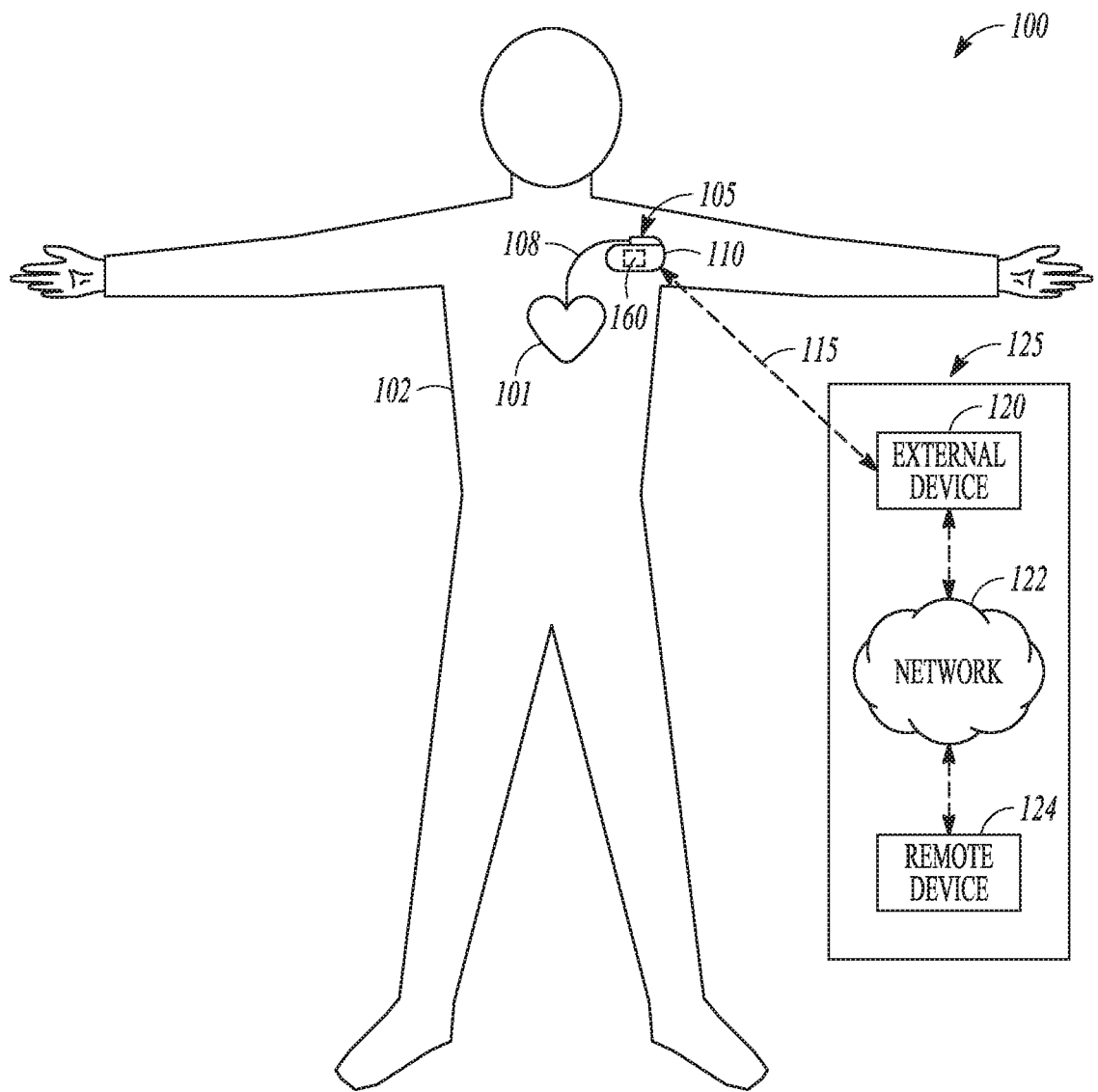
FIG. 1 illustrates generally an example of a patient management system and portions of an environment in which the patient management system may operate.

FIG. 1 illustrates generally an example of a patient management system 100 and portions of an environment in which the patient management system 100 may operate. The patient management system 100 may include an ambulatory system 105 associated with a patient body 102, an external system 125, and a telemetry link 115 providing for communication between the ambulatory system 105 and the external system 125.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices, or patient monitors, among others. The AMD 110 may alternatively or additionally include subcutaneously implanted devices such as a subcutaneous ICD or a subcutaneous diagnostic device, wearable medical devices such as patch based sensing device, or other external monitoring or therapeutic medical devices such as a bedside monitor.

The lead system 108 may include one or more transvenously, subcutaneously, or non-invasively placed leads or catheters. Each lead or catheter may include one or more electrodes for delivering pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. The arrangements and uses of the lead system 108 and the associated electrodes may be determined based on the patient need and the capability of the AMD 110. In some examples, the AMD 110 may include one or more un-tethered electrodes associated with an outer surface of the AMD 110, and the AMD 110 and the associated un-tethered electrodes may be configured to be deployed to a target cardiac site or other tissue site.

The AMD 110 may house an electronic circuit for sensing a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, intracardiac or endocardial acceleration, physical activity or exertion level, physiological response to activity, posture, respiration, body weight, or body temperature. The AMD 110 may initiate or adjust therapies based on the sensed physiological signals.

The patient management system 100 may include a worsening cardiac event detector circuit 160 provided for patient management using at least diagnostic data acquired by the ambulatory system 105. The worsening cardiac event detector circuit 160 may analyze the diagnostic data for patient monitoring, risk stratification, and detection of events such as WHF or one or more HF comorbidities. In an example as illustrated in FIG. 1, the worsening cardiac event detector circuit 160 may be substantially included in the AMD 110. Alternatively, the worsening cardiac event detector circuit 160 may be substantially included in the external system 125, or be distributed between the ambulatory system 105 and the external system 125.

The external system 125 may be used to program the AMD 110. The external system 125 may include a programmer, a communicator, or a patient management system that may access the ambulatory system 105 from a remote location and monitor patient status and/or adjust therapies. By way of example and not limitation, and as illustrated in FIG. 1, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), delivering at least one therapy, or analyzing data associated with patient health conditions such as progression of heart failure.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
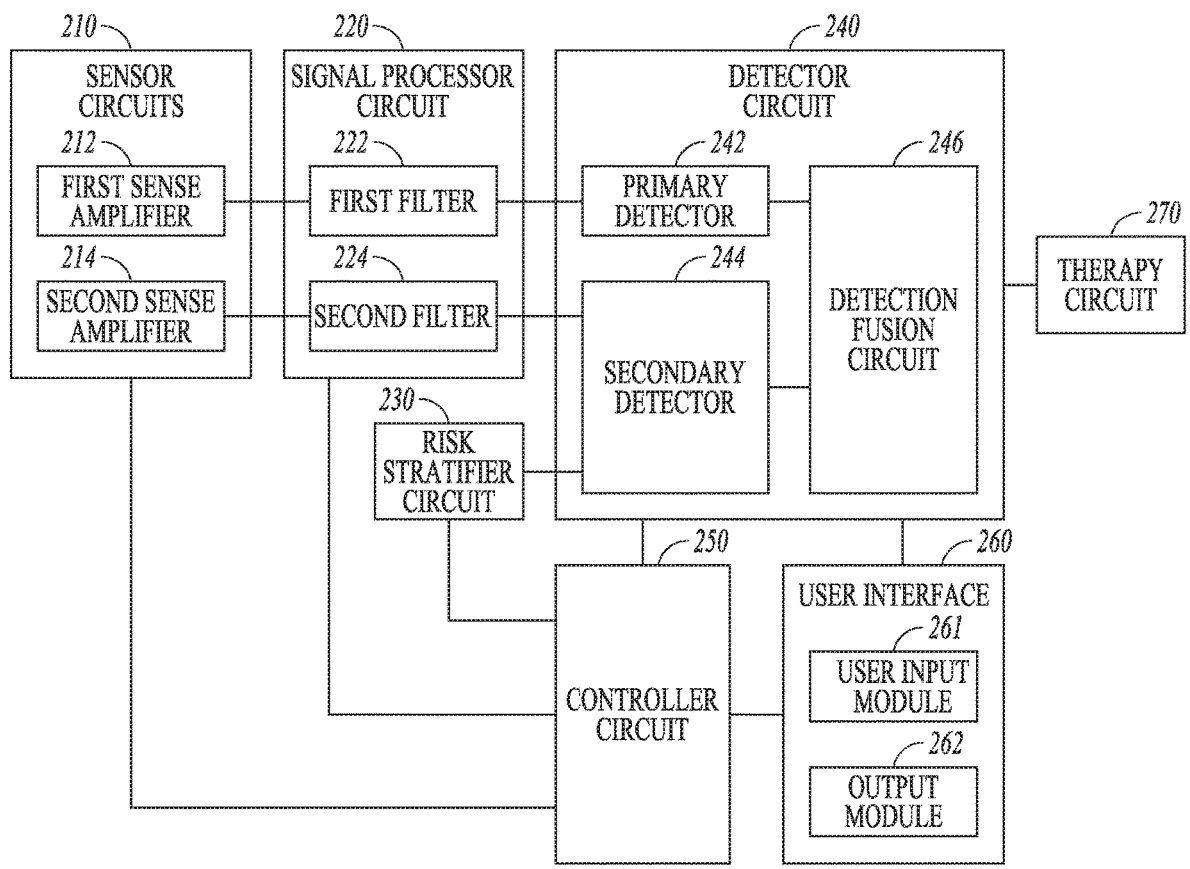
FIG. 2 illustrates generally an example of a cardiac event detection system for detecting a worsening cardiac event.

FIG. 2 illustrates generally an example of a cardiac event detection system 200 for detecting worsening cardiac conditions, such as a WHF event. The cardiac event detection system 200 may include one or more of sensor circuits 210, a signal processor circuit 220, a risk stratifier circuit 230, a detector circuit 240, a controller circuit 250, and a user interface 260. In an example, a portion of the cardiac event detection system 200 may be implemented within the AMD 110, distributed between two or more implantable or wearable medical devices (such as an implantable medical device and a subcutaneous medical device), or distributed between the AMD 110 and the external system 125.

The sensor circuits 210 may include at least a first sense amplifier circuit 212 to sense a first physiological signal and a second sense amplifier circuit 214 to sense a different second physiological signal. The first and second physiological signals may each be indicative of intrinsic physiological activities, evoked physiological activities when the heart or other tissues are stimulated in accordance with a specified stimulation configuration, or physiological activities under other specified conditions. The first or second sense amplifier circuit may be coupled to one or more electrodes such as on the lead system 108, or one or more implantable, wearable, or other ambulatory physiological sensors, to sense the physiological signal(s). Examples of physiological sensors may include pressure sensors, flow sensors, impedance sensors, accelerometers, microphone sensors, respiration sensors, temperature sensors, or blood chemical sensors, among others. Examples of the physiological signals sensed by the sensor circuits 210 may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, central venous pH value, a heart sound (HS) signal, a posture signal, a physical activity signal, or a respiration signal, among others. In some examples, the first or second sense amplifier may retrieve a respective physiological signal stored in a storage device such as an external programmer, an electronic medical record (EMR) system, or a memory unit, among other storage devices.

The signal processor circuit 220, coupled to the physiological sensor circuit 210, may include a first filter circuit 222 to filter the first sensed physiological signal to produce a trend of a first signal metric $X1_D$ for detection, and a second filter circuit 224 to filter the second sensed physiological signal to produce a trend of a second signal metric $X2_D$ for detection. The first and second signal metrics $X1_D$ and $X2_D$ may each include statistical parameters extracted from the sensed physiological signal, such as signal mean, median, or other central tendency measures or a histogram of the signal intensity, among others. The first and second signal metrics may additionally or alternatively include morphological parameters such as maximum or minimum within a specified time period such as a cardiac cycle, a specific posture or an activity intensity, positive or negative slope or higher order statistics, or signal power spectral density at a specified frequency range, among other morphological parameters.

Depending on the respective sensed physiological signal, various first and second signal metrics may be generated. In an example, a thoracic or cardiac impedance signal may be sensed using the electrodes on the lead system 108, and impedance metrics may include thoracic impedance magnitude within a specified frequency range obtained from. In an example, a heart sound (HS) signal may be sensed from an accelerometer, a microphone, or an acoustic sensor coupled to the AMD 110, and HS metrics may include intensities of first (S1), second (S2), third (S3), or fourth (S4 heart sound components or a relative intensity such as a ratio between two heart sound components, timing of one of the S1, S2, S3, or S4 heart sound components relative to a fiducial point such as a P wave, Q wave, or R wave in an ECG. In an example, the accelerometer may be associated with a lead such as of the lead system 108 or on a surface of an intracardiac pacing device located inside the heart. The accelerometer may be configured to sense intracardiac or endocardial accelerations indicative of heart sounds. In an example, a respiration signal may be sensed using an impedance sensor or an accelerometer, and the respiratory metric may include a respiratory rate, a tidal volume, a minute ventilation, a posture, or a rapid-shallow breathing index (RSBI) computed as a ratio of a respiratory rate measurement to a tidal volume measurement. In another example, a physical activity signal may be sensed using an accelerometer, and the activity metrics may include physical activity intensity, or a time duration when the activity intensity is within a specified range or above a specified threshold. In yet another example, a blood pressure signal may be sensed using a pressure sensor, and the pressure metrics may include systolic blood pressure, diastolic blood pressure, mean arterial pressure, and the timing metrics of these pressure measurements with respect to a fiducial point.

In an example, the second signal metric $X2_D$ may differ from the first signal metric $X1_D$ such that $X2_D$ may be more sensitive and less specific to a worsening cardiac event (such as a WHF event) than $X1_D$. Relative sensitivity or specificity may be based on detection performance of the signal metrics across a cohort of patients. In an example, the second signal metric $X2_D$ may be evaluated when the first signal metric $X1_D$ does not indicate a detection of worsening cardiac event. A more sensitive $X2_D$ may be used to reduce the false negative detections of the worsening cardiac event based solely on $X1_D$. In an example, the first signal metric $X1_D$ may include a HS metric such as a S3 heart sound intensity or a ratio of S3 intensity to a HS reference intensity. Examples of the reference intensity may include a first heart sound (S1) intensity, a second heart sound (S2) intensity, or heart sound energy during a specified time period within a cardiac cycle. Other examples of the second signal metric $X2_D$ may include thoracic impedance magnitude, or respiratory metric such as respiratory rate measurement, a minute ventilation measurement, a tidal volume measurement, or an RSBI.

A signal metric trend may be formed using multiple measurements of the signal metric during a specified time period. In an example, the signal metric trend may include a daily trend including daily measurement of a signal metric over a specified number of days. Each daily measurement may be determined as a central tendency of a plurality of measurements obtained within a day. In an example, a thoracic impedance trend may be generated using portions of the received impedance signal during identical phases of a cardiac cycle such as within a certain time window relative to R-wave in a ECG signal), or at identical phases of a respiratory cycle such as within an inspiration phase or an expiration phase of a respiration signal. This may minimize or attenuate the interferences such as due to cardiac or respiratory activities, in the impedance measurements. The thoracic impedance trend may be generated using impedance measurements collected during one or more impedance acquisition and analysis sessions. In an example, an impedance acquisition and analysis session may start between approximately 5 a.m. and 9 a.m. in the morning, and lasts for approximately 2-8 hours. In another example, the impedance acquisition and analysis session may be programmed to exclude certain time periods, such as night time, or when the patient is asleep. The impedance parameter may be determined as a median of multiple impedance measurements acquired during the impedance acquisition and analysis session.

The risk stratifier circuit 230 may produce a risk indication (R) indicating a risk of the patient developing a future worsening cardiac event. The risk indication may have categorical values indicating risk degrees such as "high", "medium", or "low" risks, or alternatively numerical risk scores within a specified range. The risk scores may have discrete values (e.g., integers from 0 through 5) or continuous values (e.g., real numbers between 0 and 1), where a larger risk score indicates a higher risk.

In an example, the risk indication may be at least partially automatically retrieved from a memory that stores the patient's up-to-date risk information. In an example, the risk stratifier circuit 230 may determine the risk indication by analyzing a physiological signal, such as by using one or more signal metrics generated by the signal processor circuit 220 from the physiological signal. The physiological signal or the signal metrics (denoted by $X1_R$, $X2_R$, etc.) for assessing cardiac risk may be different from the physiological signals or the signal metrics used for detecting the cardiac event (such as the first and second signal metrics $X1_D$ and $X2_D$ generated at the first and second filters 222 and 224). In another example, at least one signal metric may be used for both cardiac risk assessment and for cardiac event detection. By way of non-limiting examples, the signal metrics for cardiac risk assessment may include intensity of a heart sound component such as S3 heart sound, a respiratory rate, a tidal volume measurement, a thoracic impedance magnitude, or physical activity intensity, among others. The risk indication generated by the risk stratifier circuit 230 may be confirmed or edited by a system user such as via the user interface 260. Examples of the risk stratifier circuit for assessing a cardiac risk are discussed below, such as with reference to FIGS. 4-5.

In some examples, the risk stratifier circuit 230 may determine the risk indication using at least information about patient's overall health conditions, clinical assessments, or other current and historic diseases states that may increase or decrease the patient's susceptibility to future WHF. For example, following a WHF event, a patient may have an elevated risk of developing another WHF event or being re-hospitalized. The risk stratifier circuit 230 may determine the risk indication using time elapsed since the last WHF event. In another example, a patient having a medical history of atrial fibrillation may be more susceptible to a future WHF event. The risk stratifier circuit 230 may determine the risk indication using a trend consisting of the time spent in AF each day. In another example, the risk indication may be determined based on the number or severity of one or more comorbid conditions, such as HF comorbidities.

The detector circuit 240 may be coupled to the signal processor circuit 220 and the risk stratifier circuit 230 to detect a worsening cardiac event, such as a WHF event. The detector circuit 240 may be implemented as a part of a microprocessor circuit. The microprocessor circuit may be a dedicated processor such as a digital signal processor, application specific integrated circuit (ASIC), microprocessor, or other type of processor for processing information including the physiological signals received from the sensor circuits 210. Alternatively, the microprocessor circuit may be a general purpose processor that may receive and execute a set of instructions of performing the functions, methods, or techniques described herein.

The detector circuit 240 may include circuit sets comprising one or more other circuits or sub-circuits, such as a primary detector circuit 242, a secondary detector circuit 244, and a detection fusion circuit 246, as illustrated in FIG. 2. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The primary detector 242 may generate a primary detection indication D1 using at least the first signal metric $X1_D$. The detection may be based on temporal change of the first signal metric $X1_D$, such as a relative difference of the signal metric from a reference level representing a signal metric baseline. In an example, the relative difference may be calculated as a difference between a central tendency of multiple measurements of $X1_D$ within a short-term window and a central tendency of multiple measurements of $X1_D$ within a long-term window preceding the short-term time window in time. The relative difference may be compared to a specified condition (e.g., a threshold or a specified range), and generate a binary primary detection indication D1 of "1" if the relative difference satisfies the specified condition, or "0" if the relative fails to satisfy the specified condition. In lieu of binary detection indications, the primary detector 242 may alternatively produce the detection indication D1 having real numbers (such as between 0 and 1) indicative of confidence of detection. The confidence may be proportional to the deviation of the signal metric difference (e.g., $\Delta X1_C$) from a detection threshold.

The secondary detector 244 may generate a secondary detection indication D2 using at least the second signal metric $X2_D$ and the risk indication R. In an example, the secondary detector 244 may calculate a relative difference ($\Delta X2$) between a representative value of the second signal metric $X2_D$ such as a central tendency of multiple measurements of $X2_D$ within a short-term window and a baseline value such as a central tendency of multiple measurements of $X2_D$ within a long-term window preceding the short-term window in time. The secondary detector 244 may compute the secondary detection indication D2 using a linear, non-linear, or logical combination of the relative difference ($\Delta X2$) and the risk indication R. The relative difference ($\Delta X2$) may be modulated by the risk indications R. Similar to the primary detection indication D1, the secondary detection indication D2 may have a discrete value such as "0" indicating no detection and a "1" indicating detection of the worsening cardiac event based on $\Delta X2$, or continuous values within a specified range such as indicating the confidence of the detection. Examples of the secondary detector using the second signal metric $X2_D$ and the risk indication R are discussed below, such as with reference to FIGS. 3A-D.

The detection fusion circuit 246 may generate a composite detection indication (CDI) using the primary detection indication D1 and the secondary detection indication D2. In an example, the detection fusion circuit 246 may generate the CDI using a decision tree. The decision tree may be implemented as a set of circuits, such as logic circuit, that perform logical combinations of at least the primary and secondary detection indications D1 and D2. Alternatively, at least a portion of the decision tree may be implemented in a microprocessor circuit, such as a digital signal processor or a general purpose processor, which may receive and execute a set of instructions including logical combinations of at least the primary and secondary detection indications D1 and D2.

The decision tree for detecting the worsening cardiac event may include a tiered detection process comprising the primary detection indication D1, and subsequent detection indication D2 if the primary detection indication D1 indicates no detection of the worsening cardiac event. In an example, according to the decision tree, the CDI may be expressed as Boolean logic "OR" between D1 and D2 each satisfying respective conditions, as shown in Equation (1):

$$CDI = (D1) OR (D2) \tag{1}$$

In an example, D1 is based on a heart sound metric of a ratio of S3 to S1 heart sound intensity (S3/S1), and D2 is based on a metric of thoracic impedance magnitude (Z) or a rapid-shallow breathing index (RSBI).

As to be discussed below with reference to FIGS. 3A-D, the secondary detection indication D2 may be generated as a logical or linear combinations of the second signal metric $X2_D$ and the risk indication R. In an example, the logical combination of the risk indication (R) and the second signal metric $X2_D$ may be represented by a sub-decision tree included in the decision tree for detecting the worsening cardiac event. In an example, the risk indication is evaluated only when the second signal metric $X2_D$ indicates a detection of the worsening cardiac event (such as when $S2_D$ satisfies a detection condition). Accordingly, the secondary detection indication D2 may be represented as Boolean logic "AND" between $X2_D$ and R, that is, $D2=X2_D$ AND R. Substituting the logical formula of D2 into Equation (1) yields Equation (2) corresponding to the decision tree that includes the sub-decision tree for determining D2:

$$CDI=(X1_D)OR((X2_D)AND(R)) \qquad (2)$$

In an example, the second signal metric $X2_D$ includes the thoracic impedance (Z) and the risk indication (R) is assessed using S3 heart sound, such as a central tendency or variability of S3 intensity measurements. The CDI for detecting the worsening cardiac event may be expressed as in Equation (3) below, where T1, T2 and T3 denote thresholds for the respective signal metrics:

$$CDI = \begin{cases} 1, \text{if } \left(\frac{S3}{S1} > T1\right) \text{ OR } ((Z > T2) \text{ AND } (S3 > T3)) \\ 0, \text{else} \end{cases} \qquad (3)$$

In addition to or in lieu of the decision tree, the detection circuit 240 may generate the CDI from a composite signal trend (cY) such as a linear or a nonlinear combination of the relative difference of the first signal metric $X1_D$, and the relative difference of the second signal metric $X2_D$ modulated by the risk indications R. Examples of modulation of second signal metric may include scaling the second signal metric $X2_D$ by the risk indication R, or sampling $X2_D$ conditionally upon the risk indication R satisfying a specified condition. Modulations such as scaling and conditional sampling of $X2_D$ are discussed below with reference to FIGS. 3A-B.

To account for differences in signal properties (such as signal range or signal change or rate of change) of various signal metrics, the signal metrics may be transformed into a unified scale such that they may be easily comparable or combined. In an example, the primary detector 242 may transform the relative difference of $X1_D$ into a first sequence of transformed indices $Y1=f_1(X1_D)$. The secondary detector 244 may similarly transform the relative difference of $X2_D$ into a second sequence of transformed indices $Y2=f_2(X2_D)$ within the same specified range. In an example, the transformations $f_1$ and $f_2$ may each include a use of respective codebook that maps quantized magnitude of respective signal metric into numerical indices within a specified range, where a larger code indicates a higher signal magnitude. In an example, the transformed indices Y1 or Y2 may be obtained from a transformation of linear or nonlinear combination of more than one signal metrics.

The secondary detector 244 may modulate the transformed indices Y2 by the risk indication R, denoted by $Y2|_R$, and the detection fusion circuit 246 may generate the composite signal trend cY by combining Y1 and $Y2|_R$, such as a linear combination as shown in Equation (4) below:

$$cY=Y1+Y2|_R \qquad (4)$$

In an example, the modulation includes a multiplication operation between Y2 and R. In another example, the modulation includes conditionally-sampling of Y2 upon R satisfying a specified condition. Examples of the secondary detector using the second signal metric $X2_D$ and the risk indication R are discussed below, such as with reference to FIGS. 3A-D. The detection fusion circuit 246 may determine the CDI by comparing the composite signal trend cY to a threshold, as shown in Equation (5) below, where T1 denotes the threshold for cY:

$$CDI = \begin{cases} 1, \text{if } (Y1 + Y2|_R) > T1 \\ 0, \text{else} \end{cases} \qquad (5)$$

The controller circuit 250 may control the operations of the sensor circuits 210, the signal processor circuit 220, the risk stratifier circuit 230, the detector circuit 240, the user interface unit 260, and the data and instruction flow between these components. In an example as previously discussed, the controller circuit 250 may configure the operations of the secondary detector 243, such as a combination of the second signal metric and the risk indication for generating the secondary detection indication D2.

The user interface 260 may include a user input module 261 and an output module 261. In an example, at least a portion of the user interface unit 260 may be implemented in the external system 120. The user input module 261 may be coupled to one or more user input device such as a keyboard, on-screen keyboard, mouse, trackball, touchpad, touch-screen, or other pointing or navigating devices. The input device may enables a system user (such as a clinician) to program the parameters used for sensing the physiological signals, assessing risk indications, and detecting worsening cardiac event. The output module 262 may generate a human-perceptible presentation of the composite detection indication (CDI), such as displayed on the display. The presentation may include other diagnostic information including the physiological signals and the signals metrics, the primary and secondary detection indications, the risk indications, as well as device status such as lead impedance and integrity, battery status such as remaining lifetime of the battery, or cardiac capture threshold, among others. The information may be presented in a table, a chart, a diagram, or any other types of textual, tabular, or graphical presentation formats, for displaying to a system user. Additionally or alternatively, the CDI may be presented to the process such as an alert circuit for producing an alert in response to the CDI satisfies a specified condition. The alert may include audio or other human-perceptible media format.

In some examples, the cardiac event detection system 200 may additionally include a therapy circuit 270 configured to deliver a therapy to the patient in response to one or more of the primary or secondary detection indications or the composite detection indication. Examples of the therapy may include electrostimulation therapy delivered to the heart, a nerve tissue, other target tissues in response to the detection of the target physiological event, or drug therapy including delivering drug to a tissue or organ. In some examples, the primary or secondary detection indications or the composite detection indication may be used to modify an existing therapy, such as adjusting a stimulation parameter or drug dosage.

Figure 3A:
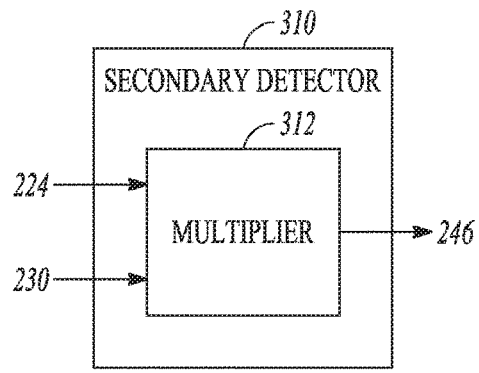
FIGS. 3A-D illustrate generally examples of secondary detectors for generating a secondary detection indication based at least on a second signal metric and the risk indication.

FIGS. 3A-D illustrate generally examples of secondary detectors 310, 320, 330 and 340 for generating a secondary detection indication (D2) based at least on a second signal metric $X2_1$ such as produced at the second filter 224 and the risk indication (R) such as produced at the risk stratifier circuit 230. The secondary detectors 310, 320, 330 and 340 may be embodiments of the secondary detector 244 in FIG. 2. The secondary detection indication D2 may be a linear or a nonlinear combination of the temporal change of a second signal metric $X2_D$ and the risk indication R. In an example as illustrated in FIG. 3A, the secondary detector 310 may include a multiplier circuit 312 that multiplies the temporal change by the risk indication R to produce the secondary detection indication D2. In an example, the risk indication R may take binary values "0" or "1", such as to gate the contribution of the second signal metric $X2_D$ to the secondary detection indication D2 e.g., using R to turn on the D2 if R=1, or to turn off D2 if R=0). In another example, the risk indication R may take real numbers such as between 0 and 1, such as to weight the contribution of the second signal metric $X2_D$ to the secondary detection indication D2. In an example, the risk indication from the risk stratifier circuit 230 includes a signal metric trend to modulate the second signal metric $X2_D$ or a transformation of a temporal change of $X2_D$, such as $Y2|_R$ as shown in Equation (4). The multiplier circuit 312 may produce a modulated second signal metric (such as Y2*R), which would be used by the detection fusion circuit 246 for generating the composite signal trend for detecting worsening cardiac event.

Figure 3B:
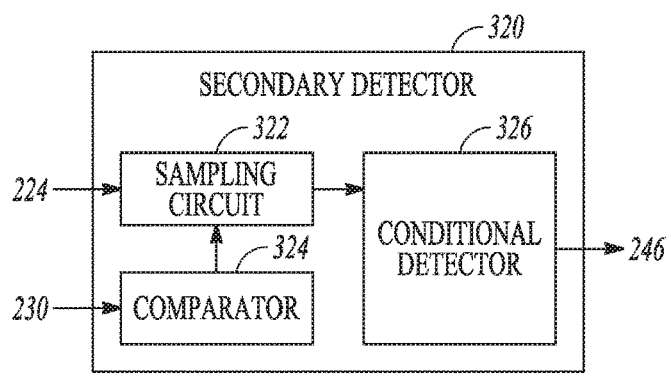

FIG. 3B illustrates the secondary detector 320 that may generate the secondary detection indication D2 using the second signal metric $X2_D$ when the risk indication satisfies a specified condition. The secondary detector 320 may include a sampling circuit 322, a comparator 324, and a conditional detector 326. The comparator 324 may compare the risk indication R to specified condition such as a specified range. The sampling circuit 322 may sample the second signal metric $X2_D$ only when the risk indication R satisfies the specified condition, such as when the signal metric used for risk assessment falls within a specified range. In an example, the second signal metric $X2_D$ may include a respiratory rate trend, and the risk indication may include physical activity intensity. The sampling circuit 322 may sample the respiratory rate trend during a time period when the physical activity intensity exceeds a specified threshold. The conditional detector 326 may generate the secondary detection indication D2 using a statistical measure, such as a central tendency or a variability, of the sampled RR measurements. In an example, the risk indication from the risk stratifier circuit 230 includes a signal metric trend to modulate the second signal metric $X2_D$ or a transformation of a temporal change of $X2_D$, such as $Y2|_R$ as shown in Equation (4). The sampling circuit 322 may produce a modulated second signal metric, including the conditionally sampled $X2_D$ or conditionally sampled transformed signal metric Y2 upon R satisfying a specified condition. The conditionally sampled $X2_D$ or Y2 would be used by the detection fusion circuit 246 for generating the composite signal trend for detecting worsening cardiac event.

Figure 3C:
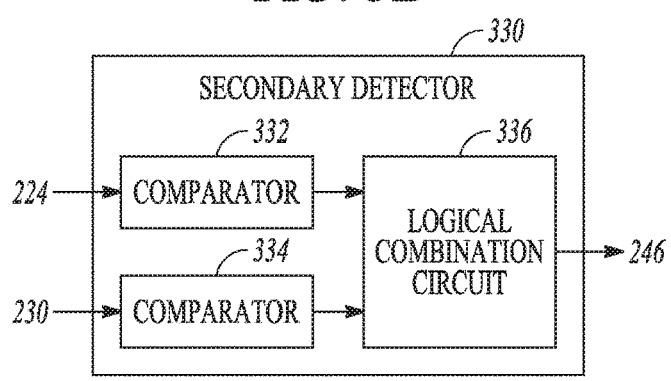

FIG. 3C illustrates the secondary detector 330 that may generate the secondary detection indication D2 using a logical combination of the second signal metric $X2_D$ and the risk indication R, such as the sub-decision tree included in the decision tree for detecting the worsening cardiac event, as previously discussed with reference to FIG. 2. The secondary detector 330 may include a comparator 332 to compare the temporal change of the second signal metric $X2_D$ to a threshold, a comparator 334 to compare the risk indication R to a threshold, and a logical combination circuit 336 to generate a detection decision based on the sub-decision tree. In an example, if the second signal metric $X2_D$ indicates a detection of the worsening cardiac event (such as falling with a range), the logical combination circuit 336 may use the risk indication R to confirm the detection based on $X2_D$. In some examples, the secondary detector 330 may additionally receive a third signal metric $X3_D$ generated from the same or a different physiological signal from which $X2_D$ is generated. The sub-decision tree may additionally include the detection according to the third signal metric $X3_D$. If the second signal metric $X2_D$ indicates no detection of the worsening cardiac event, the logical combination circuit 336 may use $X3_D$ to generate the secondary detection indication D2.

Figure 3D:
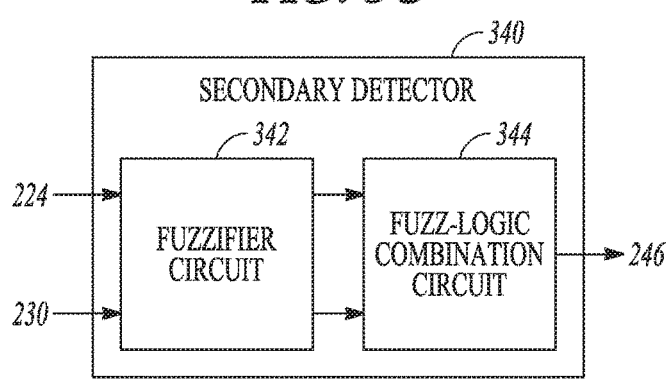

FIG. 3D illustrates the secondary detector 340 that may generate the secondary detection indication D2 using a fuzzy-logic combination of the second signal metric $X2_D$ and the risk indication R. Compared to the Boolean logic which takes crisp decisions of "1" or "0" (such as based on threshold crossing), the fuzzy-logic may take real numbers such as between 0 and 1. The fuzzifier circuit 342 may partition the range of the signal metric $X2_D$ and the range of risk indication R each into respective fuzzy sets, and to transform the second signal metric $X2_D$ and the risk indication R each into respective fuzzified representations $X2_D'$ and R'. The fuzzified presentations $X2_D'$ and R' may then be combined using fuzzy-logic operators, including "minimum" or multiplication operator corresponding to the Boolean operator "AND", "maximum" or addition operator corresponding to the Boolean operator "OR", and "1-x" (where x represents a fuzzified representation) corresponding to the Boolean operator "NOT". In an example, the fuzzy-logic combination circuit 342 may compute a numerical D2 as "minimum" between the risk indication (R) and the second signal metric $X2_D$, that is, D2=min($X2_D$, R), which corresponds to D2=$X2_D$ AND R in Boolean-logic combination as in the secondary detector 330.

In an example, the fuzzy-logic combination circuit 342 may combine the fuzzified presentations $X2_D'$ and R' using a hybrid of the Boolean logic and fuzzy-logic combinations. For example, the sub-decision tree as discussed in secondary detector 330 may include a Boolean-logic combination, such that D2=($X2_D'$) AND (R'), while the $X2_D'$ or R' may each be determined as fuzzy-logic combinations of two or more signal metrics. For example, $X2_D'$ may be determined as a maximum between a temporal change of thoracic impedance ($\Delta Z$) and a temporal change of RSBI ($\Delta RSBI$), that is, $X2_D'$=max(Z, RSBI). In an example, R' may be determined as a minimum of a central tendency or variability of S3 intensity measurements S3, and the respiratory rate (RR) variability, that is, R'=min (S3, RR). By substituting the fuzzy-logic representations of $X2_D'$ and R' into the Boolean-logic representation of D2, the secondary detection indication D2 may be determined according to Equation (6) below:

$$D2=(\max(Z,RSBI)>T1) \text{AND}(\min(S3,RR)>T2) \quad (6)$$

Figure 4:
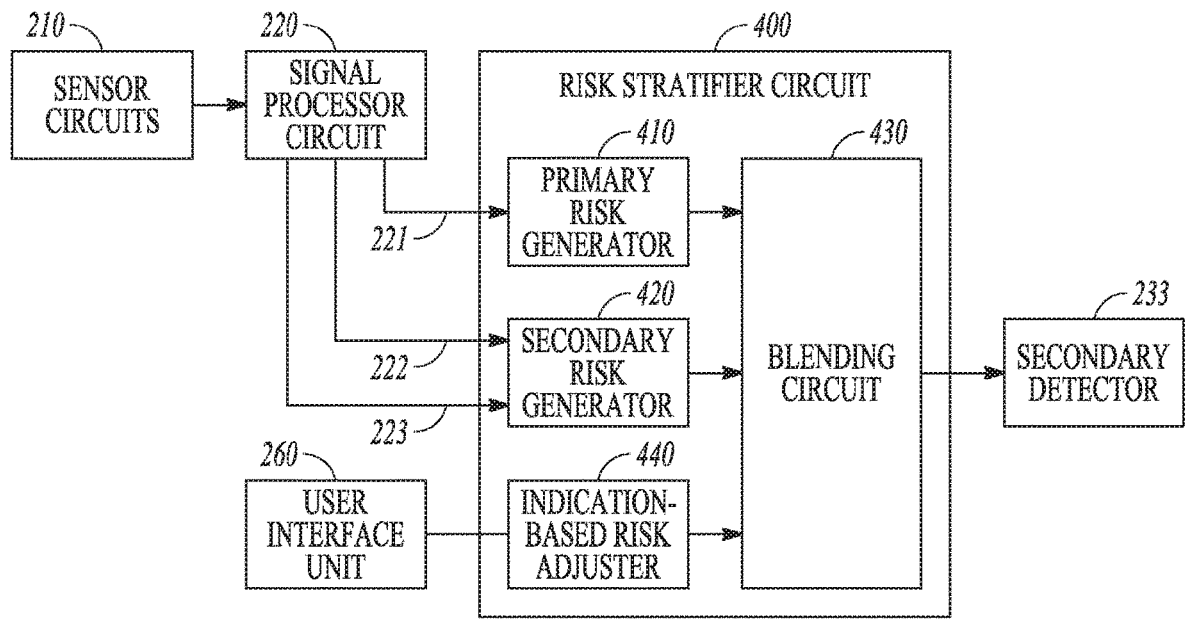
FIG. 4 illustrates generally an example of a risk stratifier circuit for assessing a patient risk of developing a future worsening cardiac event.

FIG. 4 illustrates generally an example of a risk stratifier circuit 400 for assessing a patient risk of developing a future worsening cardiac event, such as a WHF event. The risk stratifier circuit 400 may be an embodiment of the risk stratifier circuit 230. The risk stratifier circuit 400 may include one or more of a primary risk generator 410, a secondary risk generator circuit 420, an optional indication-based risk adjuster 440, and a blending circuit 430. The primary risk generator 410 may be coupled to the signal processor circuit 220 to receive a plurality of measurements of a first signal metric 221 ($X1_R$) for cardiac risk assessment, and generate a primary cardiac risk indication (R1) using at least $X1_R$. The signal metric $X1_R$ may be different from the first and second signal metrics $X1_D$ and $X2_D$ used by the primary and secondary detectors 242 and 244 for detecting worsening cardiac event. In an example, the first signal metric $X1_R$ may be extracted from a heart sound signal, and include one of a S3 intensity, or a ratio of a S3 intensity to a reference heart sound intensity such as S1 intensity, S2 intensity, or heart sound energy during a specified portion of the cardiac cycle. The primary risk generator 410 may generate the primary cardiac risk indication (R1) using a statistical measure, such as a central tendency or a variability, of the plurality of the measurements of the signal metric $X1_R$.

The secondary risk generator 420 may generate a secondary cardiac risk indication (R2) using a plurality of measurements of a second signal metric 222 ($X2_R$) and a plurality of measurements of a third signal metric 223 ($X3_R$) for cardiac risk assessment, such as generated by the signal processor circuit 220. The signal metrics $X2_R$ and $X3_R$ may be different from the signal metric $X1_R$ for cardiac risk assessment, and may be different from the signal metrics $X1_D$ and $X2_D$ for detecting worsening cardiac event. In an example, the second signal metric $X2_R$ for cardiac risk assessment may include a respiration signal metric, such as a respiratory rate, a tidal volume, or a rapid-shallow breathing index (RSBI) computed as a ratio of the respiratory rate to the tidal volume. A patient who breathes rapidly (high respiratory rate) and shallowly (low tidal volume) tends to have a high RSBI. Other examples of $X2_R$ may include thoracic impedance magnitude indicating thoracic fluid accumulation. Examples of the third signal metric $X3_R$ for cardiac risk assessment may include physical activity intensity, or a time duration when the physical activity intensity satisfies a specified condition such as above a threshold.

The secondary risk generator 420 may generate the secondary cardiac risk indication (R2) using methods similar to those used by the secondary detector 244 for generating the secondary detection indication D2 as previously discussed with reference to FIG. 2. For example, similar to the secondary detector 244 that take as input at least the second signal metric $X2_D$ and the risk indication R, the secondary risk generator 420 takes as input at least the second and third cardiac signal metrics $X2_R$ and $X3_R$ to generate the secondary cardiac risk indication (R2). In an example, R2 may be a weighted combination of the second and third cardiac signal metrics $X2_R$ and $X3_R$. In an example, R2 may be a nonlinear combination of $X2_R$ and $X3_R$, such as the second signal metric $X2_R$ weighted by the third signal metric $X3_R$. In another example, the secondary cardiac risk indication R2 may be determined using the second signal metric $X2_R$ measured during a time period when the third signal metric $X3_R$ satisfies a specified condition. Examples of sampling the second signal metric $X2_R$ conditional upon the third signal metric $X3_R$ are discussed below, such as with reference to FIG. 5. The secondary cardiac risk indication (R2) may be computed as a statistical measure, such as a central tendency or a variability, of the linearly or nonlinearly combined $X2_R$ and $X3_R$, or from the conditionally sampled $X2_R$ upon $X3_R$ satisfying a specified condition.

The blending circuit 430 may combine the primary and secondary risk indications R1 and R2 to generate a composite cardiac risk indication (cR), such as according to a fusion model. A fusion model may include one or more signal metrics and an algorithm for computing a risk indication from the one or more signal metrics. Examples of the fusion models may include a linear weighted combination, a nonlinear combination such as a decision tree, a neural network, a fuzzy-logic model, or a multivariate regression model, among others. The blending circuit 430 may generate the composite cardiac risk indication cR using a first statistic of a plurality of measurements of the signal metric $X1_R$ and a second statistic of a plurality of measurements of the combined metric between $X2_R$ and $X3_R$. Examples of the first and second statistics may each include a first-order statistic such as a central tendency measure or a second-order statistic such as a variability measure. In an example, the primary cardiac risk indication R1 includes a central tendency of a plurality of measurements of the signal metric $X1_R$, and the secondary cardiac risk indication R2 includes a variability of a plurality of measurements of the linearly or nonlinearly combined metric between $X2_R$ and $X3_R$ or conditionally sampled $X2_R$. The blending circuit 430 may generate the composite cardiac risk indication cR by combining the central tendency of $X1_R$ and the variability of $X2_R$ or the variability of the combined $X2_R$ and $X3_R$. In another example, the blending circuit 430 may generate the composite cardiac risk indication cR by combining the central tendency of $X1_R$ and the central tendency of $X2_R$ or the central tendency of the combined $X2_R$ and $X3_R$.

The risk stratifier circuit 400 may include a transformation circuit to transform the cR such as to be within a specified range (e.g., between 0 and 1). The transformation may include a linear function, a piecewise linear function, or a nonlinear function. By way of non-limiting example, the transformation circuit may transform the cR using a sigmoid function, such as provided by Equation (7):

$$cR = 1/(1+\exp(-k*cR+b)) \tag{7}$$

where "exp" denotes the exponential function, "k" is a positive number, and "b" is scalar.

In some examples, the risk stratifier circuit 400 may include a fusion model selector circuit that may select a fusion model from a plurality of candidate fusion models, and the blending circuit 430 may generate the composite cardiac risk indication cR according to the selected fusion model. The fusion model selection may be based on signal quality of the one or more physiological signals from which the cardiac signal metrics $X1_R$, $X2_R$, or $X3_R$ are generated. In an example, between a first candidate fusion model that employs a respiration signal metric and a second candidate fusion model that employs a thoracic impedance signal metric, if the respiration signal has a poor signal-to-noise ratio (SNR) or excessive variability compared to a specified signal quality criterion, or substantially out of a specified value range, then the blending circuit 430 may switch to a the second fusion model utilizing the thoracic impedance signal metric for combining the primary and secondary risk indications.

The optional indication-based risk adjuster 440 may adjust the cardiac risk indications R1 or R2 according to information about the patient clinical indications. The clinical indications may include patient medical history such as historical cardiac events, heart failure comorbidities or other concomitant disease states, exacerbation of recent chronic disease, a previous medical procedure, a clinical lab test result, patient medication intake or other treatment undertaken, patient physical assessment, or patient demographics such as age, gender, race, or ethnicity. The clinical indications may be provided by a clinician such as via the user interface 260, or stored in a memory such as an electronic medical record (EMR) system. The blending circuit 430 may generate the composite cardiac risk indication further using the patient's clinical information about the patient. In an example, the composite cardiac risk indication cR may be adjusted by the clinician such as via the user interface 260 according to the patient's clinical indications.

In some examples, the patient clinical indications may have time-varying effect on the patient risk of developing a future disease. For example, a more recent disease state or a surgery may put the patient at higher risk for developing a future worsening cardiac disease than a more remote historical disease in patient medical history. To account for the time-varying effect of the historical medical event, in an example, the indication-based risk adjuster 440 may produce time-varying weight factors decaying with time elapsed from a historical medical event, and apply the time-varying weight factors to at least one of the primary or secondary risk indications R1 or R2. The time-varying weight factor may follow a linear, exponential, or other nonlinear decay function of the time elapsed from a historical medical event. In another example, the blending circuit 430 may adjust at least one of R1 or R2 temporarily. For example, the indication-based risk adjuster 440 may be configured to maintain elevated risks of R1 or R2 above a baseline risk score within a specified timeframe following a historical medical event, and resume to the baseline risk score beyond the specified timeframe. The composite risk indication cR may be used by the secondary detector 244 to generate the second detection indication D2, as previously discussed with reference to FIG. 2.

Figure 5:
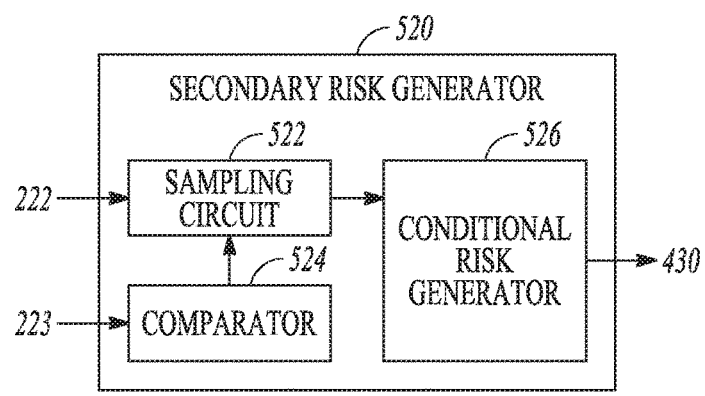
FIG. 5 illustrates generally an example of a secondary risk generator for generating a cardiac risk indication based on conditional sampling of a signal metric.

FIG. 5 illustrates generally an example of a secondary risk generator 520 for generating a cardiac risk indication based on conditional sampling of a signal metric. The secondary risk generator 520, which is an embodiment of the secondary risk generator 420 of FIG. 4, may include a sampling circuit 522 to receive a set of measurements of the second cardiac signal metric 222 ($X2_R$) from the signal processor circuit 220. The secondary risk generator 520 may include a comparator 524 to compare the third cardiac signal metric 223 ($X3_R$) to a specified threshold. The sampling circuit 522 may sample the measurements of $X2_R$ when the third signal metric $X3_R$ satisfies a specified condition. In an example, the second cardiac signal metric $X2_R$ may include a respiratory rate and the third cardiac signal metric $X3_R$ may include physical activity intensity or the duration of the physical activity above a threshold. The sampling circuit 522 may sample the respiratory rate measurements during a time period when a high physical activity is indicated, such as when the physical activity intensity exceeds a specified threshold. The conditional risk generator 526 may generate the secondary cardiac risk indication (R2) using a statistical measure, such as a central tendency or a variability, of the sampled respiratory rate measurements produced by the sampling circuit 522.

Figure 6:
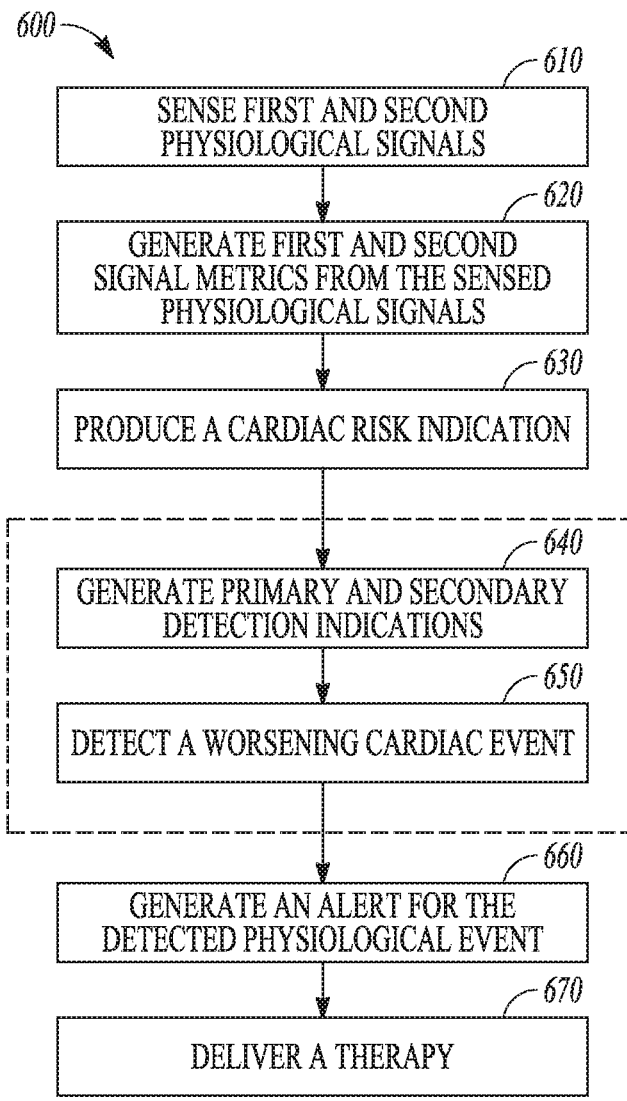
FIG. 6 illustrates generally an example of a method for detecting a worsening cardiac event.

FIG. 6 illustrates generally an example of a method 600 for detecting a worsening cardiac event. The worsening cardiac event may include events indicative of progression of cardiac condition, such as a WHF event or a HF decompensation event. The method 600 may be implemented and operate in an ambulatory medical device such as an implantable or wearable medical device, or in a remote patient management system. In an example, the method 600 may be executed by the worsening cardiac event detector 160 or any embodiment thereof, or by the external system 125.

The method 600 begins at 610 by sensing first and second physiological signals from a patient. Examples of the physiological signals may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, central venous pH value, a heart sound (HS) signal, a posture signal, a physical activity signal, or a respiration signal, among others.

At 620, at least a first signal metric may be generated from the first physiological signal and a second signal metric may be generated from the second physiological signal. The signal metric may include statistical or morphological parameters extracted from the sensed physiological signal. Examples of the signal metrics may include thoracic impedance magnitude, HS metrics such as intensities of S1, S2, S3, or S4 heart sounds or a relative intensity such as a ratio between two heart sound components, a ratio of S3 heart sound intensity to a reference heart sound intensity, timing of the S1, S2, S3, or S4 heart sound with respect to a fiducial point such as a P wave, Q wave, or R wave in an ECG, a respiratory rate, a tidal volume, a RSBI, physical activity intensity, or a time duration when the activity intensity is within a specified range or above a specified threshold, systolic blood pressure, diastolic blood pressure, mean arterial pressure, or the timing metrics of these pressure measurements with respect to a fiducial point, among others. A signal metric trend may include multiple measurements of the signal metric during a specified period of time. In an example, the signal metric trend may include a daily trend including daily measurement of a signal metric over a specified number of days.

At 630, a cardiac risk indicating a risk of the patient developing a future worsening cardiac event may be generated from one or more signal metrics of the physiological signal, such as by using the risk stratifier circuit 230 as shown in FIG. 2. The signal metrics for assessing cardiac risk may be different from the signal metrics for detecting the cardiac event. In an example, the signal metrics for cardiac risk assessment may include intensity of a heart sound component such as S3 heart sound measured from a heart sound signal, a respiratory rate or tidal volume measured from a respiration signal, thoracic impedance measured from an impedance signal such as using electrodes on one or more implantable leads and implantable device can housing, or physical activity intensity level measured from an physical activity signal such as using an ambulatory accelerometer associated with the patient. Examples of generating the cardiac risk using a plurality of signal metrics are discussed below, such as with reference to FIG. 9.

At 640, primary and secondary detection indications may be generated such as by using the detector circuit 240 as illustrated in FIG. 2. The primary detection indication D1 may be based on temporal change of at least the first signal metric from a reference level representing a signal metric baseline. In an example, a relative difference between a central tendency of the first signal metric within a short-term window and a baseline value determined within a long-term window preceding the short-term window may be determined, and a worsening cardiac event may be deemed detected if the relative difference exceeds a specified threshold. The primary detection indication D1 may have discrete or continuous values. The secondary detection indication D2 may be based on a temporal change of at least the second signal metric, such as a relative difference between a representative value of the second signal metric within a short-term time window and baseline value within a long-term time window preceding the short-term time window in time. As discussed in the examples with reference to FIGS. 3A-D, the secondary detection indication may be generated using a linear, nonlinear, or logical combination of the relative difference and the risk indication.

At 650, a worsening cardiac event may be detected using the primary and secondary detection indications. A composite detection indication (CDI) may be generated using a decision tree that includes a logical combination of the primary detection indication D1 and the secondary detection indication D2, such as a Boolean logic "OR" combination between D1 and D2. The decision tree may include a sub-decision tree representing a logical combination of the risk indication (R) and the second signal metric. In an example, the secondary detection indication D2 is a Boolean logic "AND" combination between the second signal metric and the risk indication. In various examples, at least one of the primary or secondary detection indications may include a Boolean-logic or fuzzy-logic combination of two or more signal metrics. The risk indication may similarly include a Boolean-logic or fuzzy-logic combination of two or more risk indications. Examples of the decision tree including the primary and secondary detection indications are discussed below, such as with reference to FIGS. 7A-B.

At 660, the CDI may be presented to a system user or to a process such as an alert circuit for producing an alert when the worsening cardiac event is detected. Additional information that may be displayed includes physiological signals and the signals metrics, risk indications, or primary and secondary detection indications, among others. The information may be presented in a table, a chart, a diagram, or any other types of textual, tabular, or graphical presentation formats, for displaying to a system user. The alert may include audio or other human-perceptible media format.

The method 600 may additionally include a step 670 of delivering a therapy to the patient in response to one or more of the primary or secondary detection indications or the composite detection indication. Examples of the therapy may include electrostimulation therapy delivered to the heart, a nerve tissue, other target tissues in response to the detection of the target physiological event, or drug therapy including delivering drug to a tissue or organ. In some examples, at 670, the primary or secondary detection indications or the composite detection indication may be used to modify an existing therapy, such as adjusting a stimulation parameter or drug dosage.

Figure 7A:
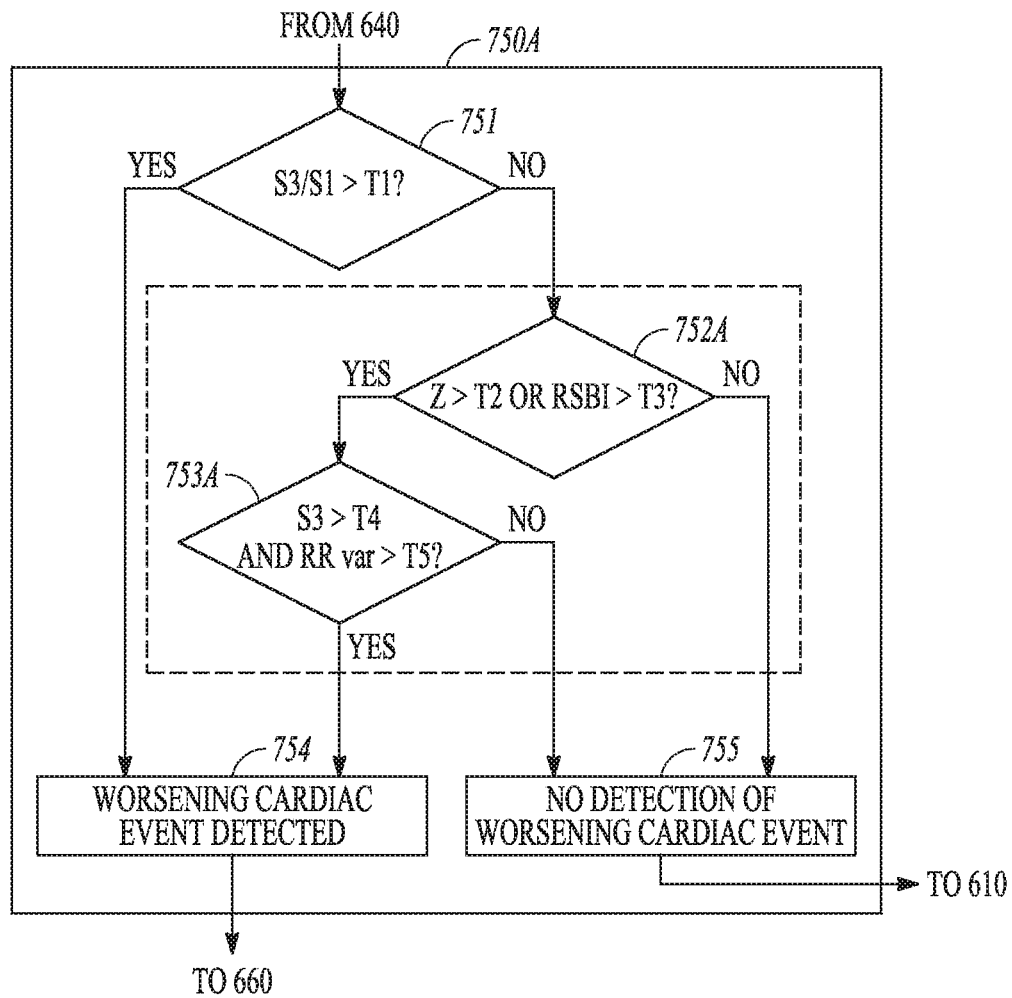
FIGS. 7A-B illustrate generally examples of decision trees for detecting the worsening cardiac event.
Figure 7B:
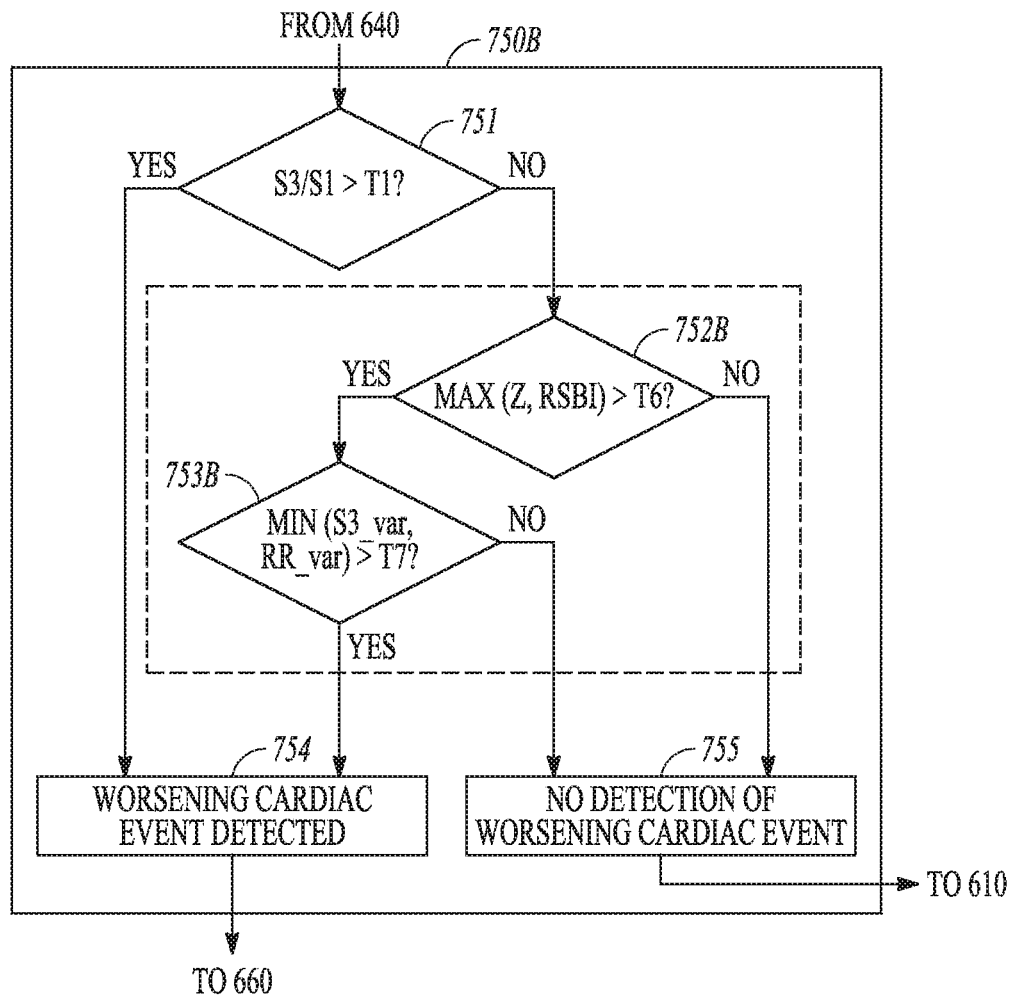

FIGS. 7A-B illustrate generally examples of decision trees 750A-B for detecting the worsening cardiac event. The decision trees 750A-B may be embodiments of the detection of the worsening cardiac event 650 in FIG. 6. The decision trees 750A-B may be implemented as a set of circuits to perform logical combinations of at least the primary and secondary detection indications. Alternatively, at least a portion of the decision tree may be implemented in a microprocessor circuit executing a set of instructions including logical combinations of at least the primary and secondary detection indications.

FIG. 7A illustrates an example of a decision tree 750A where the primary or the secondary detection indication is based on a Boolean-logic combination of two or more signal metrics. At 751, a heart sound signal metric of a ratio of S3 to S1 heart sound intensity (S3/S1) may be compared to a threshold T1 to generate a primary detection indication D1. If S3/S1 exceeds the threshold T1, then the worsening cardiac event is deemed detected at 754, corresponding to D1=1. If at 751 S3/S1 does not exceed the threshold T1, the primary detection indication D1 does not indicate a detection of worsening of cardiac event (D1=0), and a secondary detection indication D2 may be generated based on one or more second signal metrics at 752A and a risk indication determined at 753A. Steps 752A and 753A form a sub-decision tree for determining the secondary detection indication D2. The second signal metrics may be chosen from physiological signals that are more sensitive and less specific to the worsening cardiac event, such as based on detection performance of the signal metrics across a cohort of patients. A more sensitive second signal metric may reduce the false negative detection of the worsening cardiac event declared by the first signal metric. In the example illustrated in FIG. 7A, the second signal metric includes a thoracic impedance magnitude (Z) or an rapid-shallow breathing index (RSBI) as a ratio of a respiratory rate to a tidal volume measurement, both of which may be less specific and more sensitive than the S3/S1 in detecting a worsening cardiac event.

A Boolean-logic combination of Z and RSBI such as an "OR" operator may be used at 752A to determine whether the second signal metric (Z or RSBI) indicates a detection of worsening of heart failure. If either Z or RSBI exceeds the respective threshold T2 or T3, a risk indication may be generated at 753A to confirm the positive detection declared by the second signal metric. The risk indication at 753A includes a Boolean-logic combination of S3 heart sound intensity and respiratory rate (RR) variability. If both S3 and RR exceed their respective thresholds T4 and T5, then the detection of the worsening cardiac event is confirmed at 754, and the process proceeds to step 660 where an alert may be generated. However, if neither Z nor RSBI exceeds the respective threshold T2 or T3 at 752A, or if at least one of S3 or RR does not exceed the respective threshold at 753A, then the secondary detection indication D2 indicates no detection of the worsening cardiac event at 755. The process may proceed to step 610 where the physiological signal sensing and event detection processes continue as illustrated in FIG. 6.

FIG. 7B illustrates an example of a decision tree 750B where the primary or the secondary detection indication is based on a fuzzy-logic combination of two or more signal metrics. Similar to the decision tree 750A, the decision tree 750B includes a primary detection based on S3/S1 at 751 and the positive detection of worsening cardiac event at 754 if S3/S1 exceeds the threshold T1. If S3/S1 does not exceed T1, a secondary detection indication D2 may be generated using a sub-decision tree including one or more second signal metrics at 752B and a risk indication determined at 753B. In the example as illustrated in FIG. 7B, a fuzzy-logic combination such as "maximum" of Z and RSBI is performed at 752B, and a fuzzy-logic combination such as "minimum" of S3 and RR, is performed at 753B. The operator "maximum" corresponds to the Boolean logic operator "OR" at 752A, and the operator "minimum" corresponds to the Boolean logic operator "AND" at 753A. In an example, the two or more signal metrics in 752B (Z and RSBI) or 753B (S3 and RR) may be transformed into respective fuzzified presentations, and the fuzzy-logic combination at 752B or 753B may be applied to the fuzzified presentations of the respective signal metrics. If max(Z, RSBI) exceeds the threshold T6 at 752A, and min(S3, RR) exceeds the threshold T7 at 753B, then the detection of the worsening cardiac event is confirmed at 754, and the process proceeds to step 660 to generate an alert of the detected worsening cardiac event. However, if max (Z, RSBI) does not exceed the threshold T6 at 752B, or if min (S3, RR) does not exceed the threshold T7 at 753B, then the secondary detection indication D2 indicates no detection of the worsening cardiac event at 755; and the process proceeds to step 610 where the physiological signal sensing and event detection processes continue as illustrated in FIG. 6.

Figure 8:
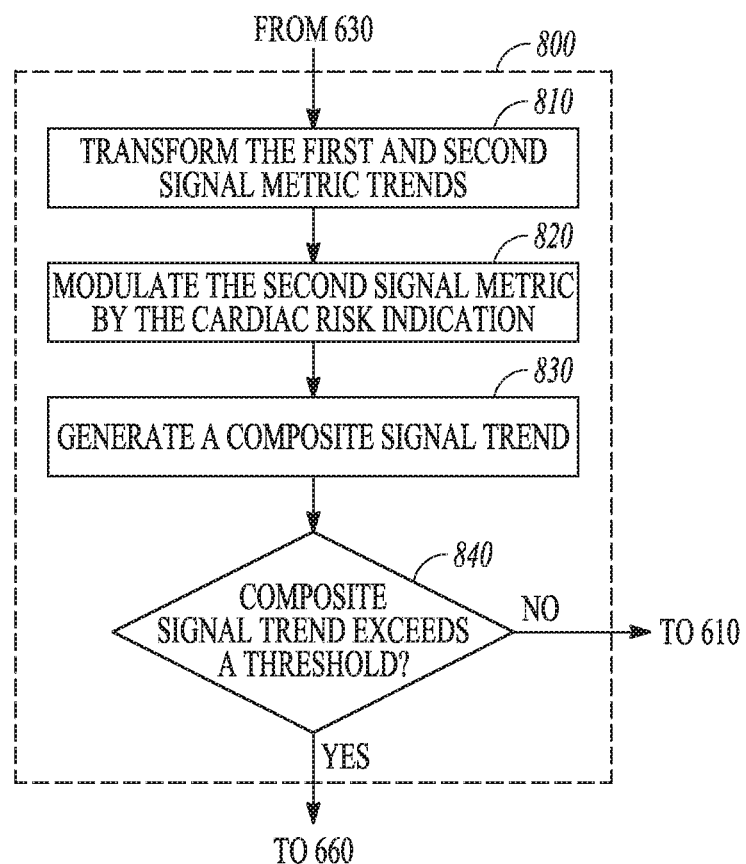
FIG. 8 illustrates generally an example of a portion of a method for detecting worsening cardiac event based at least the first and second signal metrics.

FIG. 8 illustrates generally an example of a portion of a method 800 for detecting a worsening cardiac event based at least on the first and second signal metrics. The method 800 may be in addition to or as an alternative of the steps 640 and 650 for detecting worsening cardiac event based on the primary and secondary detection indications. At 810, the first and second signal metric trends, such as those generated at 620, may be transformed into a unified scale. In an example, a temporal change of the first signal metric (such as a relative difference between a short-term window and a baseline value computed from a long-term window) may be transformed into a first sequence of transformed indices within a specified range. A temporal change of the second signal metric may similarly be transformed into a second sequence of transformed indices within the same specified range, such that the transformed first and second signal metric trends may be easily compared or combined. In an example, the transformation of the first and second signal metric trend may be based on respective codebook that maps quantized magnitude of respective signal metric into numerical indices within a specified range, where a larger code indicates a higher signal magnitude. In an example, the transformed indices may be obtained from a transformation of linear or nonlinear combination of more than one signal metrics.

At 820, the second signal metric may be modulated by the cardiac risk indication. In an example, the modulation of the second signal metric may include a scaled temporal change of the second signal metric weighted by the risk indication. As illustrated in FIG. 3A, the risk indication may take discrete values such as "0" or "1", such as to gate the contribution of temporal change to the secondary detection indication. The risk indication R may alternatively take real numbers such as between 0 and 1, and weight the contribution of temporal change to the secondary detection indication. In another example, the modulation of the second signal metric may include a sampled temporal change of the second signal metric when the risk indication satisfies a specified condition. In an example as illustrated in FIG. 3B, the second signal metric may include a respiratory rate trend, and the risk indication may include a physical activity intensity. The respiratory rate trend may be sampled during a time period when the physical activity intensity exceeds a specified threshold, and the secondary detection indication may be determined as a statistical measure, such as a central tendency or a variability, of the conditionally sampled RR measurements.

At 830, a composite signal trend cY may be generated using the transformed first signal metric Y1 and the second signal metric Y2 modulated by R. The combination may include a linear or nonlinear combination, such as shown in Equation (4) as previously discussed. In an example, the composite signal trend cY is a linear combination of Y1 and Y2*R. In another example, the composite signal trend cY is a linear combination of Y1 and conditionally-sampled Y2 upon R satisfying a specified condition. The composite signal trend cY may then be compared to a threshold at 840. If cY exceeds the threshold, then the worsening cardiac event is deemed detected, and an alert is generated at 660. If cY does not exceed the threshold, then no worsening cardiac event is deemed detected, and the process may proceed to step 610 where the physiological signal sensing and event detection processes continue as illustrated in FIG. 6. In an example, an alert can be generated if cY exceeds a first threshold. The alert may sustain until cY falls below a second threshold indicating a recovery or improvement of the physiological status.

Figure 9:
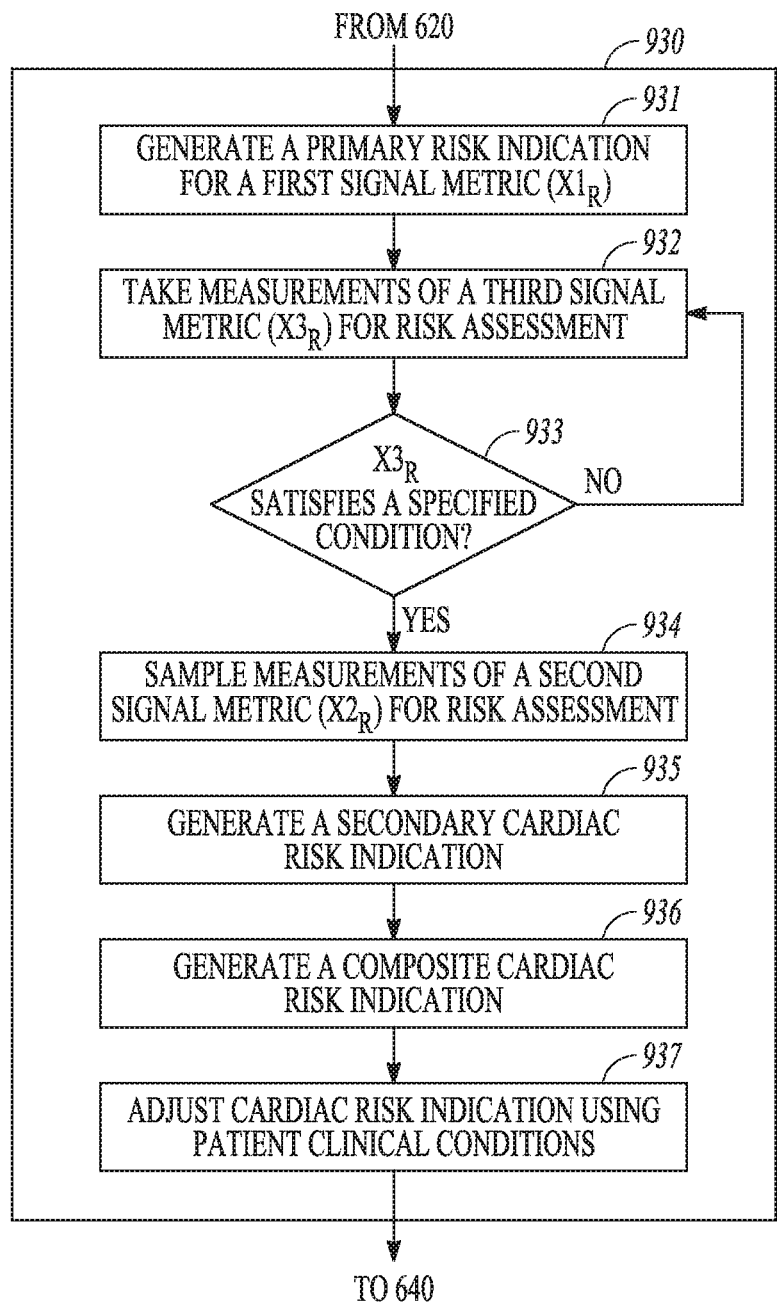
FIG. 9 illustrates generally an example of a method for cardiac risk assessment.

FIG. 9 illustrates generally an example of a method 930 for cardiac risk assessment. The method 930 may be an embodiment of the step 630 of FIG. 6, and may be implemented in and executed by the risk stratifier circuit 230 of FIG. 2 or the risk stratifier circuit 400 of FIG. 4.

The method 930 begins at 931 by generating a primary risk indication for cardiac risk assessment from a first signal metric ($X1_R$) for cardiac risk assessment. The signal metric $X1_R$ may be different from the signal metrics used for detecting worsening cardiac event. In an example, the first signal metric $X1_R$ may be extracted from a heart sound signal, and include one of a S3 intensity, or a ratio of a S3 intensity to a reference heart sound intensity such as one of S1 intensity, S2 intensity, or heart sound energy during a specified portion of the cardiac cycle. In an example, the primary cardiac risk indication may include a statistical measure, such as a central tendency a variability, of the plurality of the measurements of the signal metric $X1_R$.

At 932, a plurality of measurements of a third signal metric 223 ($X3_R$) for cardiac risk assessment may be taken. $X3_R$ may be different from the signal metric $X1_R$ for cardiac risk assessment. At 933, the $X3_R$ may be compared to a specified condition (such as a threshold) to control a conditional sampling of a second signal metric $X2_R$. If $X3_R$ satisfies the specified condition, a plurality of measurements of the second signal metric $X2_R$ may be sampled at 934. In an example, the second cardiac signal metric $X2_R$ may include a respiratory rate and the third cardiac signal metric $X3_R$ may include physical activity intensity or the duration of the physical activity above a threshold. The respiratory rate measurements may be sampled during a time period when a high physical activity is indicated, such as when the physical activity intensity exceeds a specified threshold. Other examples of the signal metric $X2_R$ may include a tidal volume, a rapid-shallow breathing index (RSBI) computed as a ratio of the respiratory rate to the tidal volume, or a thoracic impedance magnitude indicating thoracic fluid accumulation, among others. Other examples of $X3_R$ may include time of day, metabolic state, or heart rate, among others.

At 935, a secondary cardiac risk indication may be generated. An example of the secondary cardiac risk indication may include a statistical measure, such as a central tendency or a variability, of the sampled respiratory rate measurements.

At 936, the primary and secondary risk indications R1 and R2 may be combined to generate a composite cardiac risk indication (cR), such as according to a fusion model. The fusion model may include one or more signal metrics and an algorithm for transforming the one or more signal metrics into a risk indication. Examples of the fusion models may include a linear weighted combination, a nonlinear combination such as a decision tree, a neural network, a fuzzy-logic model, or a multivariate regression model, among others. In an example, a fusion model may be selected according signal quality of the one or more physiological signals from which the cardiac signal metrics $X1_R$, $X2_R$, or $X3_R$ are generated. For example, a first candidate fusion model that employs a physiological signal with a higher signal-to-noise ratio (SNR) may be selected over a second candidate fusion model that employs a physiological signal with a lower SNR. The composite cardiac risk indication cR may be generated by combining a first statistic of a plurality of measurements of the signal metric $X1_R$ and a second statistic of a plurality of measurements of the combined metric between $X2_R$ and $X3_R$. Examples of the first and second statistics may each include a first-order statistic such as a central tendency measure or a second-order statistic such as a variability measure. In an example, the primary cardiac risk indication R1 includes a central tendency or other first-order statistics of a plurality of measurements of the signal metric $X1_R$, and the secondary cardiac risk indication R2 includes a variability or other second-order statistics of a plurality of measurements of the linearly or nonlinearly combined metric between $X2_R$ and $X3_R$ or conditionally sampled $X2_R$. The composite cardiac risk indication cR may be generated by combining the central tendency of $X1_R$ and the variability of the $X2_R$ or the variability of the combined $X2_R$ and $X3_R$.

At 937, the cardiac risk indications R1 or R2 may be adjusted according to information about the patient clinical indications. The clinical indications may include patient medical history such as historical cardiac events, heart failure comorbidities or other concomitant disease states, exacerbation of recent chronic disease, a previous medical procedure, a clinical lab test result, patient medication intake or other treatment undertaken, patient physical assessment, or patient demographics such as age, gender, race, or ethnicity. In an example, the composite cardiac risk indication cR may be adjusted by the clinician. In an example, at least one of the primary or secondary risk indications R1 or R2 may be weighted by time-varying weight factors that decay with time elapsed from a historical medical event may be applied to. The time-varying weight factor may follow a linear, exponential, or other nonlinear decay function of the time elapsed from a historical medical event. In another example, at least one of R1 or R2 may be adjusted temporarily. For example, an elevated risks of R1 or R2 above a baseline risk score may be applied within a specified timeframe following a historical medical event, and resume to the baseline risk score beyond the specified timeframe. The composite risk indication cR may then be used to generate the second detection indication at 640.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system comprising:
a signal processor circuit configured to:
receive a first physiological signal;
generate a first signal metric from the first physiological signal;
receive a second physiological signal different from the first physiologic signal; and
generate a second signal metric, different from the first signal metric, from the second physiological signal;
a detector circuit configured to:
receive a risk indication indicating a cardiac risk of the patient;
generate a primary detection indication of a presence or absence of a worsening cardiac event based on the first signal metric;
generate a secondary detection indication of a presence or absence of the worsening cardiac event, different from the primary detection indication, based on the second signal metric;
modulate the secondary detection indication by the risk indication; and detect the worsening cardiac event as a combination of (1) the unmodulated primary detection indication and (2) the modulated secondary detection indication; and an output circuit configured to generate an alert in response to the detection of the worsening cardiac event.

2. The system of claim 1, further comprising a therapy circuit configured to deliver a therapy in response to the detection of the worsening cardiac event.

3. The system of claim 1, wherein the first signal metric includes a heart sound signal metric and the second signal metric includes a respiratory signal metric, wherein the heart sound signal metric includes a third heart sound (S3) intensity or a ratio of a third heart sound (S3) intensity to a reference heart sound intensity; and wherein the respiratory signal metric includes a respiration rate measurement, a tidal volume measurement, or a ratio of the respiration rate to the tidal volume measurement.

4. The system of claim 1, wherein the detector circuit is configured to detect the worsening cardiac event using a decision tree including the primary detection indication and the modulated secondary detection indication, wherein the detector circuit is configured to modulate the secondary detection indication using a sub-decision tree included in the decision tree, the sub-decision tree including the risk indication and the secondary detection indication.

5. The system of claim 4, wherein the signal processor circuit is configured to receive a third physiological signal different from the first and second physiological signals, and wherein the detector circuit is configured to:

generate a third detection indication using the third physiological signal and the sub-decision tree; and if the modulated secondary detection indication indicates no detection of the worsening cardiac event, detect the worsening cardiac event based on a combination of the primary detection indication and the third detection indication.

6. The system of claim 1, wherein:

at least one of the primary or secondary detection indication includes a Boolean-logic or fuzzy-logic combination of two or more signal metrics; or the risk indication includes a Boolean-logic or fuzzy-logic combination of two or more risk indications.

7. The system of claim 1, wherein the detector circuit is configured to:

modulate the second signal metric by the risk indication;

generate a composite signal trend using a combination of the first signal metric and the modulated second signal metric; and detect the worsening cardiac event in response to the composite signal trend satisfying a specified condition.

8. The system of claim 7, wherein the composite signal trend includes a linear combination of a temporal change of the first signal metric and a temporal change of the modulated second signal metric, the modulated second signal metric including:

the temporal change of the second signal metric weighted by the risk indication; or the temporal change of the second signal metric sampled when the risk indication satisfies a specified condition.

9. The system of claim 1, wherein the risk indication includes a composite cardiac risk indication, the system comprising:

a risk stratifier circuit configured to:

generate a primary cardiac risk indication using at least the first signal metric;

generate a secondary cardiac risk indication using at least the second signal metric; and generate the composite cardiac risk indication using at least one of the primary cardiac risk indication or the secondary cardiac risk indication.

10. The system of claim 9, wherein:

the signal processor circuit is configured to receive a third physiological signal different from the first and second physiological signals, and to generate a third signal metric from the third physiological signal; and the risk stratifier circuit is to generate a secondary cardiac risk indication using a plurality of measurements of the second signal metric during a time period when the third signal metric satisfies a specified condition.

11. The system of claim 9, wherein:

the signal processor circuit is to generate a first plurality of measurements of the first signal metric and a second plurality of measurements of the second signal metric; and the risk stratifier circuit is to:

generate the primary cardiac risk indication including a first statistic of the first plurality of measurements of the first signal metric, and the secondary cardiac risk indication including a second statistic of the second plurality of measurements of the second signal metric; and generate the composite cardiac risk indication using a combination of the first statistic of the first signal metric and the second statistic of the second signal metric.

12. The system of claim 9, further comprising a fusion model selector circuit configured to select a fusion model from a plurality of candidate fusion models based on signal quality of the first and second physiological signals, wherein the risk stratifier circuit is configured to generate the composite cardiac risk indication using both the primary and secondary cardiac risk indications according to the selected fusion model.

13. A method comprising:

receiving, via a signal processor circuit, first and second physiological signals;

generating, via the signal processor circuit, a first signal metric from the first physiological signal and a second signal metric from the second physiological signal;

receiving, via a detector circuit, a risk indication indicating a cardiac risk of the patient;

generating, via the detector circuit, a primary detection indication of a presence or absence of a worsening cardiac event based on the first signal metric, and a secondary detection indication of a presence or absence of the worsening cardiac event based on the second signal metric;

modulating, via the detector circuit, the secondary detection indication by the risk indication; and detecting, via the detector circuit, the worsening cardiac event as a combination of (1) the unmodulated primary detection indication, and (2) the modulated secondary detection indication.

14. The method of claim 13, wherein detecting the worsening cardiac event includes using a decision tree including the primary detection indication and the modulated secondary detection indication, wherein modulating the secondary detection indication includes using a sub-decision tree of the decision tree, the sub-decision tree including the risk indication and the secondary detection indication.

15. The method of claim 14, wherein:
at least one of the primary or secondary detection indication includes a Boolean-logic or fuzzy-logic combination of two or more signal metrics; or
the risk indication includes a Boolean-logic or fuzzy-logic combination of two or more risk indications.

16. The method of claim 14, further comprising:
modulating the second signal metric by the risk indication;
generating a composite signal trend using a combination of the first signal metric and the modulated second signal metric; and
detecting the worsening cardiac event in response to the composite signal trend satisfying a specified condition.

17. The method of claim 16, wherein modulating the second signal metric includes weighting a temporal change of the second signal metric by the risk indication, or sampling a temporal change of the second signal metric when the risk indication satisfies a specified condition.

18. The method of claim 13, wherein the risk indication includes a composite cardiac risk indication, the method comprising:
generating a primary cardiac risk indication using at least a first signal metric for cardiac risk assessment;
generating a secondary cardiac risk indication using at least a second signal metric for cardiac risk assessment; and
generating a composite cardiac risk indication using both the primary and secondary cardiac risk indications.

19. The method of claim 18, comprising receiving a third physiological signal different from the first and second physiological signals, and generating a third signal metric from the third physiological signal, wherein generating the secondary cardiac risk indication includes taking a plurality of measurements of the second signal metric during a time period when the third signal metric satisfies a specified condition.

20. A system comprising:
a signal processor circuit configured to:
receive first physiological information;
generate a first signal metric from the first physiological information;
receive second physiological information different from the first physiologic information; and
generate a second signal metric, different from the first signal metric, from the second physiological information;
a detector circuit configured to:
receive a risk indication indicating a cardiac risk of the patient;
generate a first detection indication of a presence or absence of a worsening cardiac event based on the first signal metric;
generate a second detection indication of a presence or absence of a worsening cardiac event, different from the first detection indication; and
detect the worsening cardiac event as a combination of the first detection indication, irrespective of the risk indication, and a combination of the second signal metric and the risk indication; and
an output circuit configured to generate an alert in response to the detection of the worsening cardiac event.

* * * * *